US009637537B2

United States Patent
Kwang et al.

(10) Patent No.: US 9,637,537 B2
(45) Date of Patent: May 2, 2017

(54) MONOCLONAL ANTIBODIES TARGETING NEUTRALIZING EPITOPES ON H7 INFLUENZA VIRUSES

(71) Applicant: TEMASEK LIFE SCIENCES LABORATORY LIMITED, Singapore (SG)

(72) Inventors: Hwei-Sing Jimmy Kwang, Singapore (SG); Fang He, Singapore (SG); Rajesh Kumar Subaschandrabose, Singapore (SG)

(73) Assignee: TEMASEK LIFE SCIENCES LABORATORIES LIMITED, Singapore (SG)

( * ) Notice: Subject to any disclaimer, the term of this patent is extended or adjusted under 35 U.S.C. 154(b) by 0 days.

(21) Appl. No.: 14/442,626

(22) PCT Filed: Aug. 23, 2013

(86) PCT No.: PCT/SG2013/000366
§ 371 (c)(1),
(2) Date: May 13, 2015

(87) PCT Pub. No.: WO2014/077777
PCT Pub. Date: May 22, 2014

(65) Prior Publication Data
US 2016/0257731 A1   Sep. 8, 2016

Related U.S. Application Data

(60) Provisional application No. 61/727,927, filed on Nov. 19, 2012.

(51) Int. Cl.
*C07K 16/10* (2006.01)
*G01N 33/569* (2006.01)
*A61K 39/00* (2006.01)

(52) U.S. Cl.
CPC ... *C07K 16/1018* (2013.01); *G01N 33/56983* (2013.01); *A61K 2039/505* (2013.01); *A61K 2039/544* (2013.01); *A61K 2039/545* (2013.01); *C07K 2317/21* (2013.01); *C07K 2317/33* (2013.01); *C07K 2317/34* (2013.01); *C07K 2317/76* (2013.01); *G01N 2333/11* (2013.01)

(58) Field of Classification Search
CPC .......... A61K 2039/505; A61K 39/145; A61K 39/12; A61K 39/42; A61K 2039/525; A61K 38/162; C12N 7/00; C12N 2760/16134; C12N 2760/16122; C12N 2760/16234; C12N 2760/16151; C12N 2760/16022; C07K 2317/55; C07K 14/7051; C07K 14/005; C07K 16/1018
See application file for complete search history.

(56) References Cited

U.S. PATENT DOCUMENTS

2011/0274702 A1   11/2011   Lanzavecchia

FOREIGN PATENT DOCUMENTS

WO   2009/035420 A1   3/2009

OTHER PUBLICATIONS

He F, Soejoedono RD, Murtini S, Goutama M, Kwang J. Complementary monoclonal antibody-based dot ELISA for universal detection of H5 avian influenza virus. BMC Microbiol. Dec. 30, 2010;10:330.*
He Q, Velumani S, Du Q, Lim CW, Ng FK, Donis R, Kwang J. Detection of H5 avian influenza viruses by antigen-capture enzyme-linked immunosorbent assay using H5-specific monoclonal antibody. Clin Vaccine Immunol. May 2007;14(5):617-23. Epub Mar. 7, 2007.*
Fouchier RAM, Munster V, Rimmelzwaan GF, Osterhaus AD. Influenza A virus (A/Netherlands/219/03(H7N7)) hemagglutinin (HA) gene, partial cds. GenBank: AY338459.1. Dep. May 14, 2004.*
Fouchier RAM, Munster V, Rimmelzwaan GF, Osterhaus AD. Hemagglutinin, partial [Influenza A virus (A/Netherlands/219/2003(H7N7))]. GenBank: AAR02640.1. Dep. May 14, 2004.*
Fouchier RA, Schneeberger PM, Rozendaal FW, Broekman JM, Kemink SA, Munster V, Kuiken T, Rimmelzwaan GF, Schutten M, Van Doornum GJ, Koch G, Bosman A, Koopmans M, Osterhaus AD. Avian influenza A virus (H7N7) associated with human conjunctivitis and a fatal case of acute respiratory distress syndrome. Proc Natl Acad Sci U S A. Feb. 3, 2004;101(5):135.*
Bowie JU, Reidhaar-Olson JF, Lim WA, Sauer RT. Deciphering the message in protein sequences: tolerance to amino acid substitutions. Science. Mar. 16, 1990;247(4948):1306-10.*
Velumani, S. et al., "Development of an Antigen-Capture ELISA for Detection of H7 Subtype Avian Influenza from Experimentally Infected Chickens," Journal of Virological Methods, Feb. 2008, vol. 147, Issue 2, pp. 219-225.
Yang, M. et al., "Evaluation of Diagnostic Applications of Monoclonal Antibodies Against Avian Influenza H7 Viruses," Clinical and Vaccine Immunology, Sep. 2010, vol. 17, No. 9, pp. 1398-1406.
Mueller, M. et al., "Antigenic Characterization of Recombinant Hemagglutinin Proteins Derived from Different Avian Influenza Virus Subtypes," PLoS ONE, Feb. 2010, vol. 5, Issue 2, e9097, 9 pages.

(Continued)

*Primary Examiner* — Rachel B Gill
(74) *Attorney, Agent, or Firm* — Rothwell, Figg, Ernst & Manbeck, P.C.

(57) ABSTRACT

The present invention relates to the murine monoclonal antibody (mAb) 11B9 and to mAb 62 each of which target major neutralizing epitopes of influenza A H7 hemagglutinin and active fragments thereof. The present invention also relates to methods and compositions for the prophylaxis and treatment of H7 influenza using murine mAb 11B9, mAb 62 or fragments thereof. The present invention further relates to methods and kits for determining, identifying and/or quantifying (a) influenza A hemagglutinin in a sample or vaccine or (b) an antibody against influenza A hemagglutinin.

47 Claims, 6 Drawing Sheets

(56) References Cited

OTHER PUBLICATIONS

Figure 1A:
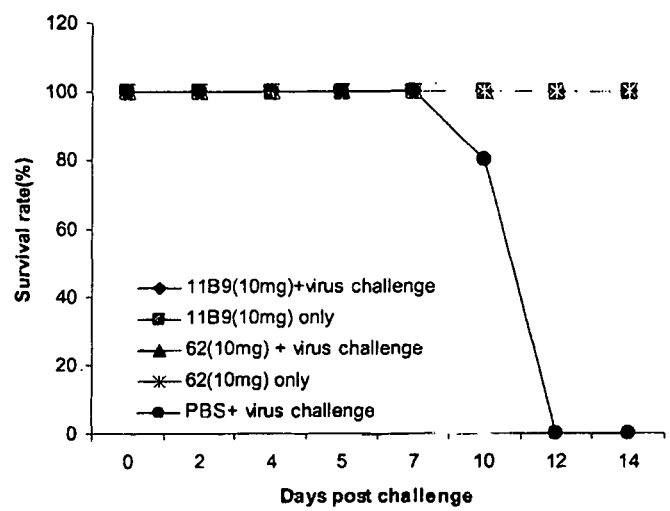

He, F. et al., "Effective Intranasal Therapeutics and Prophylactics with Monoclonal Antibody Against Lethal Infection of H7N7 Influenza Virus," Antiviral Research, published online Aug. 13, 2013, vol. 100, Issue 1, pp. 207-214.
International Search Report mailed Nov. 11, 2013, PCT/SG2013/000366, Filing Date: Aug. 23, 2013, Applicant: Temasek Life Sciences Laboratory Limited, 5 pages.
Written Opinion dated Aug. 31, 2016 from the Intellectual Property Office of Singapore in counterpart Application No. 11201503878X, 6pages.

\* cited by examiner

MONOCLONAL ANTIBODIES TARGETING NEUTRALIZING EPITOPES ON H7 INFLUENZA VIRUSES

CROSS-REFERENCE TO RELATED APPLICATIONS

The present application is a national stage filing under 35 U.S.C. §371 of PCT/SG2013/000366, filed on 23 Aug. 2013, and is related to and claims priority to U.S. Provisional Patent Application Ser. No. 61/727,927, filed 19 Nov. 2012. Each application is incorporated herein by reference.

SEQUENCE SUBMISSION

The present application is being filed along with a Sequence Listing in electronic format. The Sequence Listing is entitled 2577226PCTSequenceListing.txt, created on 9 Aug. 2013 and is 13 kb in size. The information in the electronic format of the Sequence Listing is incorporated herein by reference in its entirety.

BACKGROUND OF THE INVENTION

The present invention relates to the murine monoclonal antibody (mAb) 11B9 and to mAb 62 each of which target major neutralizing epitopes of influenza A H7 hemagglutinin and active fragments thereof. The present invention also relates to methods and compositions for the prophylaxis and treatment of H7 influenza using murine mAb 11B9, mAb 62 or fragments thereof. The present invention further relates to methods and kits for determining, identifying and/or quantifying (a) influenza A hemagglutinin in a sample or vaccine or (b) an antibody against influenza A hemagglutinin.

The publications and other materials used herein to illuminate the background of the invention or provide additional details respecting the practice, are incorporated by reference, and for convenience are respectively grouped in the Bibliography.

Occurrence of highly pathogenic avian influenza (HPAI) subtype H7 in poultry continues to be a public health concern (Jadhao et al., 2008; Abbas et al., 2011). Influenza A H7 subtype viruses from both Eurasian and North American lineages have resulted in more than 100 cases of human infection since 2002 in the Netherlands, Italy, Canada, the United Kingdom, and the United States. In 2003, an HPAI H7N7 outbreak in the Netherlands infected 89 people in close contact with affected poultry and resulted in one fatal case. These cases include outbreaks of HPAI H7N7 virus in the Netherlands in 2003 that resulted in more than 80 cases of human infection and one fatality; HPAI H7N3 virus in British Columbia, Canada, in 2004 that resulted in two cases of conjunctivitis; a cluster of human infections of low-pathogenicity avian influenza (LPAI) H7N2 virus in the United Kingdom in 2007 that resulted in several cases of influenza-like illness and conjunctivitis; and a single case of respiratory infection in New York in 2003. H7 subtype viruses have presented significant pandemic potential (Min et al., 2010).

Humans are immunologically naïve to the H7 avian influenza viruses, and LPAI H7 subtype viruses circulating in domestic poultry and wild birds in Eurasia and North America have the potential to evolve and acquire an highly pathogenic phenotype either by accumulating mutations or by recombination at the hemagglutinin (HA) cleavage site resulting in a highly cleavable HA that is a virulence motif in poultry. Recent work also suggests that contemporary North American lineage H7 subtype viruses, isolated in 2002 to 2003, are partially adapted to recognize 2-6-linked sialic acids, which are the receptors preferred by human influenza viruses and are preferentially found in the human upper respiratory tract (Gambaryan et al., 2012). Moreover, coinfection and genetic reassortment of RNA genomes between H7 avian influenza viruses and human influenza viruses, including the seasonal H1N1 and H3N2 and pandemic H1N1 viruses, could result in the generation of reassortant viruses with the capacity to efficiently transmit among people and result in a pandemic. Domesticated birds may serve as important intermediate hosts for the transmission of wild-bird influenza viruses to humans, as may pigs, as evidenced by human infections with swine-origin 2009 pandemic H1N1 influenza virus throughout the world.

Passive immunotherapy using monoclonal antibodies has been viewed as a viable option for treatment of many infectious diseases. Currently, there has been a lot of focus on therapeutic approaches using neutralizing antibodies against the HA1 protein of the influenza virus (Prabakaran et al., 2009). This protein is easy to target as it is on the surface of the virus and antibodies against this protein can neutralize the virus efficiently. Hence, monoclonal antibodies against neutralizing epitopes of H7 hemagglutinin (HA) may be an attractive alternative to active vaccination of humans, in particular for those individuals who are at high risk from influenza infection, such as the immuno-compromised patients or the elderly who do not respond well to active immunization. It is important that any mAb product should offer broad protection against circulating strains of H7 influenza.

It is desired to identify monoclonal antibodies that can be used for the prophylaxis and treatment of H7 influenza.

SUMMARY OF THE INVENTION

The present invention relates to the murine monoclonal antibody (mAb) 11B9 and to mAb 62 each of which target major neutralizing epitopes of influenza A H7 hemagglutinin and active fragments thereof. The present invention also relates to methods and compositions for the prophylaxis and treatment of H7 influenza using murine mAb 11B9, mAb 62 or fragments thereof. The present invention further relates to methods and kits for determining, identifying and/or quantifying (a) influenza A hemagglutinin in a sample or vaccine or (b) an antibody against influenza A hemagglutinin.

Thus, in a first aspect, the present invention provides a monoclonal antibody specific to a major neutralizing epitope of influenza H5 hemagglutinin and active fragments thereof, i.e., antigen binding fragments (also referred to herein as antibody fragments). In one embodiment, the monoclonal antibody or fragment thereof specifically binds to a conformational epitope of H7 hemagglutinin (HA), wherein the conformational epitope is comprised of amino acids 136Ser, 137Gly and 227Glu of the full length HA protein including the signal protein of H7N7(A/Netherlands/219/03). The full length coding sequence is set forth in SEQ ID NO:1 which corresponds to nucleotides 22-1710 of the sequence set forth in GenBank Accession No. AY338459 which also includes 5' and 3' flanking sequences. The full length protein sequence is set forth in SEQ ID NO:2. In another embodiment, the monoclonal antibody or fragment thereof specifically binds to a conformational epitope of H7 hemagglutinin to which murine mAb 11B9 specifically binds. In an additional embodiment, the monoclonal antibody is murine mAb 11B9. In a further embodiment, the monoclonal antibody is murine mAb 11B9 produced by murine hybridoma 11B9.

In one embodiment, the monoclonal antibody or fragment thereof specifically binds to a conformational epitope of H7 hemagglutinin (HA), wherein the conformational epitope is comprised of amino acids 175Lys and 227Glu of the full length HA protein including the signal protein. In another embodiment, the monoclonal antibody or fragment thereof specifically binds to a conformational epitope of H7 hemagglutinin to which murine mAb 62 specifically binds. In an additional embodiment, the monoclonal antibody is murine mAb 62. In a further embodiment, the monoclonal antibody is murine mAb 62 produced by murine hybridoma 62.

In another embodiment, the present invention provides a nucleic acid encoding a monoclonal antibody or antigen binding fragment thereof described herein. In one embodiment the nucleic acid encodes the murine mAb 11B9 or mAb 62 or antigen binding fragment thereof. In an additional embodiment, the present invention provides a vector comprising the nucleic acid. In a further embodiment, the present invention proves a cell comprising and expressing the vector.

In a second aspect, the present invention provides methods and compositions for the prophylaxis and treatment of H5N1 influenza using murine monoclonal antibody mAb 11B9 or mAb 62 or fragments thereof. In one embodiment, the present invention provides a pharmaceutical composition comprising a monoclonal antibody described herein and a pharmaceutically acceptable diluent or carrier. In some embodiments, the monoclonal antibody is murine mAb 11B9 or mAb 62. In another embodiment, the pharmaceutical composition comprises an antigen binding fragment of a monoclonal antibody described herein and a pharmaceutically acceptable diluent or carrier. In some embodiments, the antigen binding fragment is an antigen binding fragment of murine mAb 11B9 or mAb 62. In an additional embodiment, the pharmaceutical composition comprises a nucleic acid molecule encoding said antibody or antibody fragment and a pharmaceutically acceptable diluent or carrier. In a further embodiment, the pharmaceutical composition comprises a vector comprising said nucleic acid and a pharmaceutically acceptable diluent or carrier. In another embodiment, the pharmaceutical composition comprises a cell expressing said vector and a pharmaceutically acceptable diluent or carrier. In an additional embodiment, the pharmaceutical composition comprises a nucleic acid molecule encoding said antibody or antibody fragment and a pharmaceutically acceptable diluent or carrier. In a further embodiment, the pharmaceutical composition comprises a vector comprising said nucleic acid and a pharmaceutically acceptable diluent or carrier. In another embodiment, the pharmaceutical composition comprises a cell expressing said vector and a pharmaceutically acceptable diluent or carrier.

In one embodiment, the present invention provides a method of reducing influenza H7 virus infection in a subject, or lowering the risk of influenza H7 virus infection in a subject, inhibiting infection of a subject by one or more influenza H7 virus strains, or prophylaxis of influenza infection or disease by one or more influenza H7 virus strains. In this embodiment, the method comprises administering to a subject in need thereof, a therapeutically effective amount of a monoclonal antibody or an antigen binding fragment thereof described herein, a nucleic acid molecule comprising a polynucleotide encoding said antibody or antibody fragment; a vector comprising said polynucleotide; or a cell expressing said vector. In some embodiments, the monoclonal antibody is murine mAb 11B9 or mAb 62. In one embodiment, the subject is immunocompromised, is an infant, is a young child or is elderly. In another embodiment, administration provides a therapeutic benefit. In an additional embodiment, therapeutic benefit comprises inhibiting increases in influenza virus titer, decreasing influenza virus titer, inhibiting increases in influenza virus replication, decreasing influenza virus replication, inhibiting increases in influenza virus proliferation or decreasing influenza virus proliferation, or decreasing progression, severity, frequency, duration or probability one or more symptoms or complications associated with influenza virus infection in a subject. In one embodiment, a symptom or complication is selected from chills, fever, cough, sore throat, nasal congestion, sinus congestion, nasal infection, sinus infection, body ache, head ache, fatigue, pneumonia, bronchitis, ear infection, ear ache and death. In another embodiment, the therapeutic benefit comprises hastening a subject's recovery from influenza H7 virus infection. In a further embodiment, the agent that is administered to the subject is administered prior to, substantially contemporaneously with or following influenza H7 virus infection of the subject.

In a third aspect, the present invention provides methods and compositions for the identification, characterization and/or quantification of H7 expression using a monoclonal antibody or fragments thereof described herein. In some embodiments, the monoclonal antibody is murine mAb 11B9 or mAb 62. In one embodiment, the H7 expression relates to the expression of HA of H7 influenza viruses. In one embodiment, the composition comprises a monoclonal antibody or fragments thereof described herein. In some embodiments, the monoclonal antibody is murine mAb 11B9 or mAb 62. In another embodiment, the method comprises detecting the binding of the H7 with a monoclonal antibody or fragments thereof described herein. In some embodiments, the monoclonal antibody is murine mAb 11B9 or mAb 62. In one embodiment, the invention relates to immunofluorescence assays (IFA), immunohistochemical assays and other methods that utilize such binding proteins, including ELISA, hemagglutination inhibition (HI) assays and virus neutralization (VN) assays. In one embodiment, a dual function ELISA assay as described herein can be utilized.

In some embodiments, the methods and compositions for the identification and/or quantification of H7 expression are for the identification and/or quantification of an immunogenic agent of an H7 virus in a vaccine. In one embodiment, the immunogenic agent comprises a hemagglutinin or antigenic portion thereof or a nucleic acid encoding the hemagglutinin or antigenic portion thereof. In another embodiment, the antigenic portion includes an epitope of hemagglutinin. In one embodiment, the immunogenic agent is a virus comprising hemagglutinin. In another embodiment, the virus is inactivated. In an additional embodiment, the virus is an attenuated virus. In another embodiment, the virus is in the form of a virosome. In a further embodiment, the virus is egg-derived or cell culture-derived. In another embodiment, the immunogenic agent is a split virus comprising hemagglutinin or a split virus antigenic preparation. In one embodiment, the immunogenic agent is hemagglutinin or antigenic portion thereof. In another embodiment, the hemagglutinin or antigenic portion thereof has been isolated. In an additional embodiment, the hemagglutinin or antigenic portion thereof is produced by an expression system. In one embodiment, the expression system is any expression system, such as a viral expression vector in which the hemagglutinin or antigenic portion thereof is presented or displayed on the surface of the virus. In one embodiment, the viral expression vector is any viral expression vector such as a modified vaccinia virus expression vector, an adenovirus expression vector, a poxvirus expression vector, a baculovirus expression vector and the like. In one embodiment, the expression vector is a baculovirus expression vector and the virus presenting or displaying the hemagglutinin or antigenic portion thereof is a baculovirus. In another embodiment, the immunogenic agent is a nucleic acid encoding the hemagglutinin or antigenic portion thereof which is capable of expression in the subject.

In a fourth aspect, the present invention provides kits and methods for the detection of an influenza A H7 subtype virus in a biological specimen or for the detection of an antibody to an influenza A H7 hemagglutinin (referred to herein as an anti-H7 antibody) in a biological specimen. In one embodiment for the detection of an influenza A H7 subtype virus in a biological specimen, the method comprises contacting the specimen with a first antibody which is a monoclonal antibody or antibody fragment thereof as described herein (sometimes referred to as a capture antibody). In another embodiment, the method further comprises contacting the specimen with a second antibody or antibody fragment thereof as described herein that specifically binds to an epitope of H7 hemagglutinin of an influenza A H7 subtype virus in which the second antibody contains or is conjugated to a detectable element (sometimes referred to as a detector antibody). In one embodiment for the detection of an antibody to an influenza A H7 hemagglutinin in a biological specimen, the method comprises contacting the specimen to which a control H7 hemagglutinin of an influenza A H7 subtype virus (sometimes referred to herein as a control H7 antigen) has been added with a first antibody which is a monoclonal antibody or antibody fragment thereof as described herein (sometimes referred to as a capture antibody). In another embodiment, the method further comprises contacting the specimen with a second antibody or antibody fragment thereof as described herein that specifically binds to an epitope of H7 hemagglutinin of an influenza A H7 subtype virus in which the second antibody contains or is conjugated to a detectable element (sometimes referred to as a detector antibody). In some embodiments, the second antibody contains a radioactive atom, is conjugated to a fluorescent molecule, or is conjugated to an enzyme. In other embodiments, the first antibody is immobilized on a solid surface. In some embodiments, the first monoclonal antibody is murine mAb 11B9 or mAb 62. In other embodiments, the second monoclonal antibody is mAb 11B9 or mAb 62. In one embodiment, the control H7 antigen is a recombinant H7 antigen. In another embodiment, the control H7 antigen is a H7 surface expressing virus, such as a baculovirus. In one embodiment, the invention relates to immunofluorescence assays (IFA), immunohistochemical assays and other methods that utilize such monoclonal antibodies or related binding proteins, including ELISA, hemagglutination inhibition (HI) assays and virus neutralization (VN) assays. In one embodiment, a dual function ELISA assay as described herein can be utilized.

In one embodiment, the assay is a dual function ELISA that is effective for both antigen and antibody detection of H7 avian influenza virus. In one embodiment, one of mAb 11B9 or mAb 62 is used as the capture antibody and the other of mAb 11B9 or mAb 62 is used as the detector antibody. In one embodiment, the capture antibody is coated on a solid phase, such as a microtiter plate, a microbead, or the like. To detect antigen in a biological sample, the sample is contacted with the capture antibody for a period of time sufficient to allow any H7 antigens in the sample to bind to the capture antibody. The detector antibody is then contacted with the bound sample H7 antigens, if any, for a period of time sufficient to allow the dectector antibody to bind to the bound sample H7 antigens. The binding of any detector antibody is then determined in order to determine the presence and/or the amount of H7 antigens in the sample. To detect anti-H7 antibody in a biological sample, a control H7 antigen is added to a biological sample to prepare a mixture. In one embodiment, a fixed amount of the control H7 antigen is added to the biological sample. The control H7 antigen binds to any anti-H7 antibody that may be present in the biological sample. The mixture is then contacted with the capture antibody for a period of time sufficient to allow the control H7 antigen to bind to the capture antibody. If anti-H7 antibodies are present in the biological, some of the control H7 antigen bound to the capture antibody will be bound to anti-H7 antibodies and some of the control H7 antigen bound to the capture antibody will be free from bound antibodies. In one embodiment, the control H7 antigen is a recombinant H7 antigen. In another embodiment, the control H7 antigen is a H7 surface expressing virus, such as a baculovirus. The detector antibody is then contacted with any bound control H7 antigen not bound by sample H7 antibodies, if any, for a period of time sufficient to allow the dectector antibody to bind to the bound control H7 antigen not bound by sample H7 antibodies. The binding of detector antibody is then determined in order to determine the presence and/or the amount of H7 antibodies in the sample. In one embodiment, a reduced level of bound detector antibody is indicative of the presence of anti-H7 antibodies in the biological sample.

In one embodiment, the kit comprises a first antibody which is a monoclonal antibody or antibody fragment thereof described herein together with instructions for performing an assay to detect the influenza A H7 subtype virus. In some embodiments, the monoclonal antibody is murine mAb 11B9 or mAb 62. In another embodiment, the kit further comprises a second antibody that specifically binds to an epitope of H7 hemagglutinin of an influenza A virus in which the second antibody contains or is conjugated to a detectable element. In some embodiments, the second antibody is mAb 11B9 or mAb 62. In some embodiments, the second antibody contains a radioactive atom, is conjugated to a fluorescent molecule, or is conjugated to an enzyme. In other embodiments, the first antibody is immobilized on a solid surface. In another embodiment, the kit further comprises an H7 hemagglutinin antigen. In some embodiments, the H7 hemagglutinin antigen is a recombinant H7 protein. In other embodiments, the H7 hemagglutinin antigen is a H7 surface expressing virus, such as a baculovirus. In one embodiment, the kits are useful for identifying and/or quantifying an immunogenic agent of an H7 virus in a vaccine. In another embodiment, the kits are useful for detecting an H7 hemagglutinin or an antibody against an H7 hemagglutinin in a biological sample. In one embodiment, the invention relates to immunofluorescence assays (IFA), immunohistochemical assays and other methods that utilize such monoclonal antibodies or related binding proteins, including ELISA, hemagglutination inhibition (HI) assays and virus neutralization (VN) assays. In some embodiments, a dual function ELISA assay as described herein can be utilized.

BRIEF DESCRIPTION OF THE FIGURES

FIGS. 1A and 1B show the prophylactic efficacy of mAb 11B9 and 62 in mice against H7N7 virus. FIG. 1A: The results are expressed in terms of percent survival. PBS was used as a negative control. FIG. 1B: The results are expressed in terms of percent body weight (at the beginning of the trial). PBS was used as a negative control.

Figure 2:
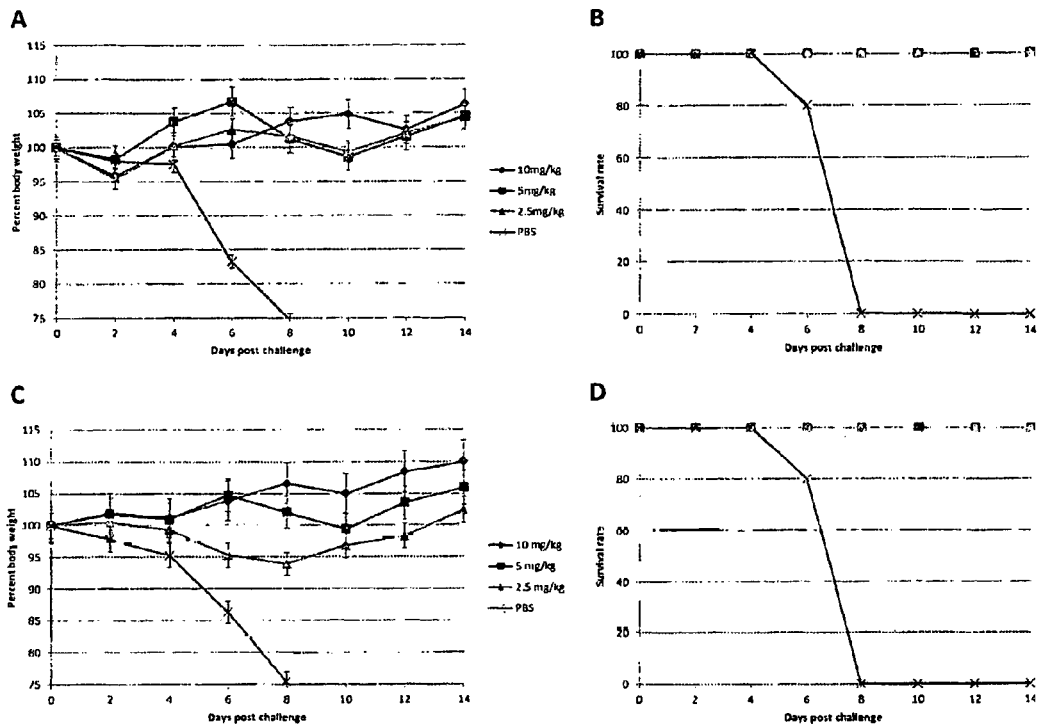

FIGS. 2A-2D show prophylactic efficacy of mAb 62 against H7 challenge in mice. FIGS. 2A and 2B: Groups of mice (n=5) were pre-treated intranasally with 2.5 mg/kg, 5 mg/kg, 10 mg/kg or 0 mg/kg (PBS) of mAb 62. FIGS. 2C and 2D: Groups of mice (n=5) were pre-treated intraperitoneally with 5 mg/kg, 10 mg/kg or 0 mg/kg (PBS) of mAb 62, one day before challenge with $5MLD_{50}$ of mouse-adapted HPAI H7N7 (A/Netherlands/219/03, RG). Mice were monitored for survival and weight loss throughout a 14 day observation period. The results are expressed in terms of percent survival (FIGS. 2C and 2D) and percent body weight (FIGS. 2A and 2B) (at the beginning of the trial) respectively.

FIGS. 3A and 3B show therapeutic efficacy of mAb 62 against H7 challenge in mice. Groups of mice (n=5) were infected with 5MLD50 of mouse-adapted HPAI H7N7 (A/Netherlands/219/03, RG). One day post-challenge, the mice were treated via intraperitoneal route with 15 mg/kg of mAb 62, or via intranasal route with 5 mg/kg, 10 mg/kg, 15 mg/kg or 0 mg/kg (PBS) of mAb 62. Mice were monitored for survival and weight loss throughout a 14 day observation period. The results are expressed in terms of percent survival (FIG. 3B) and percent body weight (FIG. 3A) (at the beginning of the trial) respectively.

FIGS. 4A and 4B show therapeutic efficacy of two doses of mAb 62 against H7 challenge in mice. Groups of mice (n=5) were infected with 10MLD50 of mouse-adapted HPAI H7N7 (A/Netherlands/219/03, RG). One day, two days, or seven days post-challenge, the mice were treated once or twice via intransal route with 10 mg/kg or 0 mg/kg (PBS) of mAb 62. Mice were monitored for survival and weight loss throughout a 14 day observation period. The results are expressed in terms of percent survival (FIG. 4B) and percent body weight (FIG. 4A) (at the beginning of the trial) respectively. dpi: days post infection.

FIGS. 5A-5E show histopathology of lung tissue in passively treated mice. Photomicrographs of hematoxylin and eosin stained lungsections of mice treated with mAb 62 (15 mg/kg) either via intranasal or intraperitoneal route after post experimental viral infection with $5MLD_{50}$ of HPAI H7N7 (A/Netherlands/219/03, RG). FIG. 5A: Lung section from mice intranasally treated with mAb 62 collected on 14 days postinfection. FIG. 5B: Lung section from mice intraperitoneal treated with mAb 62 collected on 14 days postinfection. FIG. 5C: Lung section from infected mice without treatment collected on 6 days postinfection. FIG. 5D: Lung section from infected mice without treatment collected on 8 days postinfection. FIG. 5E: Lung section from uninfected mice.

FIG. 6 shows measurement of viral infectivity titers in the lungs of passively treated mice. Mice treated with mAb 62 (15 mg/kg) either via intranasal or intraperitoneal route after experimental viral infection with $5MLD_{50}$ of HPAI H7N7 (A/Netherlands/219/03, RG). Lung samples were collected on 2 days, 4 days, 6 days and 14 days post infection. The results of virus load in lungs were expressed in terms of mean value of $\log_{10} TCID_{50}/g$. "#" represents no survival of any animals in the group. (*, P<0.05; , P<0.01; *, P<0.001; n=5; for points of the intranasal group as compared with the intraperitoneal counterpart.)

FIG. 7 shows the procedures of both antigen and antibody detection in the dual function ELISA.

FIG. 8 shows the specificity of H7 antigen detection in the dual ELISA. The specificity of H7 antigen detection in the dual-ELISA was examined with 100 μl of PBS containing the H7 strains adjusted to an HA titer of 8 or non-H7 viruses with HA titers of ≥16. Values represent the means of absorbances of duplicate wells from two independent tests. OD 490: optical density at 490 nm; dotted line: cut-off values; Blank AF: allantoic fluid without virus.

FIG. 9 shows theensitivity of H7 antigen detection in the dual ELISA. Tested viruses with an HA titer of 16 were twofold diluted and subjected to the dual ELISA for antigen detection. Values represent the means of absorbance of duplicate wells from two independent tests. OD 490: optical density at 490 nm; dotted line: cut-off values.

FIG. 10 shows the specificity of H7 antibody detection in the dual ELISA. Sera from different animals immunized with different subtypes of influenza viruses were collected 10 days after the 2nd immunization and normalized to a HI titer of 16 before tested in the dual ELISA. Inhibition above the cut-off value of 30% blocking was considered as positive; i.e. antibodies to H7 were present. The results were expressed as the arithmetic mean of percent blocking values. aH7N7: A/duck/Hokkaido/1/10; Ck: chicken; Gp: guinea pig; Ms: mouse; Bac: wildtype baculovirus immunized serum; Blank: preimmune serum. Dotted line: cut-off values.

DETAILED DESCRIPTION OF THE INVENTION

The present invention relates to the murine monoclonal antibody (mAb) 11B9 and to mAb 62 each of which target major neutralizing epitopes of influenza A H7 hemagglutinin and active fragments thereof. The present invention also relates to methods and compositions for the prophylaxis and treatment of H7 influenza using murine mAb 11B9, mAb 62 or fragments thereof. The present invention further relates to methods and kits for determining, identifying and/or quantifying (a) influenza A hemagglutinin in a sample or vaccine or (b) an antibody against influenza A hemagglutinin.

By "isolated" is meant a biological molecule free from at least some of the components with which it naturally occurs.

The terms "antibody" or "antibodies" as used herein are art-recognized terms and are understood to refer to molecules or active fragments of molecules that bind to known antigens, particularly to immunoglobulin molecules and to immunologically active portions of immunoglobulin molecules, i.e., molecules that contain a binding site that specifically binds an antigen. An immunoglobulin is a protein comprising one or more polypeptides substantially encoded by the immunoglobulin kappa and lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Also subclasses of the heavy chain are known. For example, IgG heavy chains in humans can be any of IgG1, IgG2, IgG3 and IgG4 subclass. The immunoglobulin according to the invention can be of any class (IgG, IgM, IgD, IgE, IgA and IgY) or subclass (IgG1, IgG2, IgG3, IgG4, IgA1 and IgA2) of immunoglobulin molecule.

As used herein "specifically binds" in reference to an antibody means that the antibody binds to its target antigen with greater affinity that it does to a structurally different antigen(s).

A typical immunoglobulin structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as full length intact antibodies or as a number of well-characterized fragments produced by digestion with various peptidases or chemicals. Thus, for example, pepsin digests an antibody below the disulfide linkages in the hinge region to produce F(ab')$_2$, a dimer of Fab which itself is a light chain joined to $V_H$—CH$_1$ by a disulfide bond. The F(ab')$_2$ may be reduced under mild conditions to break the disulfide linkage in the hinge region thereby converting the F(ab')$_2$ dimer into an. Fab' monomer. The Fab' monomer is essentially a Fab fragment with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that any of a variety of antibody fragments may be synthesized de novo either chemically or by utilizing recombinant DNA methodology. Thus, the term antibody, as used herein also includes antibody fragments either produced by the modification of whole antibodies or synthesized de novo or antibodies and fragments obtained by using recombinant DNA methodologies.

"Antibodies" are intended within the scope of the present invention to include chimeric or humanized monoclonal antibodies, as well as active fragments thereof. Examples of active fragments of molecules that bind to known antigens include separated light and heavy chains, Fab, Fab/c, Fv, Fab', and F(ab')$_2$ fragments, including the products of an Fab immunoglobulin expression library and epitope-binding fragments of any of the antibodies and fragments mentioned above.

These active fragments can be derived from an antibody of the present invention by a number of techniques. For example, monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw et al. (1982); Rousseaux et al. (1986).

Recombinantly made antibodies may be conventional full length antibodies, active antibody fragments known from proteolytic digestion, unique active antibody fragments such as Fv or single chain Fv (scFv), domain deleted antibodies, and the like. An Fv antibody is about 50 Kd in size and comprises the variable regions of the light and heavy chain. A single chain Fv ("scFv") polypeptide is a covalently linked VH::VL heterodimer which may be expressed from a nucleic acid including VH- and VL-encoding sequences either joined directly or joined by a peptide-encoding linker. See Huston et al. (1988). A number of structures for converting the naturally aggregated, but chemically separated light and heavy polypeptide chains from an antibody V region into an scFv molecule which will fold into a three dimensional structure substantially similar to the structure of an antigen-binding site. See, e.g. U.S. Pat. Nos. 5,091,513; 5,132,405 and 4,956,778.

The combining site refers to the part of an antibody molecule that participates in antigen binding. The antigen binding site is formed by amino acid residues of the N-terminal variable ("V") regions of the heavy ("H") and light ("L") chains. The antibody variable regions comprise three highly divergent stretches referred to as "hypervariable regions" or "complementarity determining regions" (CDRs) which are interposed between more conserved flanking stretches known as "framework regions" (FRs). In an antibody molecule, the three hypervariable regions of a light chain (LCDR1, LCDR2, and LCDR3) and the three hypervariable regions of a heavy chain (HCDR1, HCDR2 and HCDR3) are disposed relative to each other in three dimensional space to form an antigen binding surface or pocket. The antibody combining site therefore represents the amino acids that make up the CDRs of an antibody and any framework residues that make up the binding site pocket.

The identity of the amino acid residues in a particular antibody that make up the combining site can be determined using methods well known in the art. See, e.g., U.S. Patent Application Publication No. 2010/0080800. The identity of the amino acid residues in a particular antibody that are outside the CDRs, but nonetheless make up part of the combining site by having a side chain that is part of the lining of the combining site (i.e., it is available to linkage through the combining site), can be determined using methods well known in the art such as molecular modeling and X-ray crystallography. See e.g., Riechmann et al. (1988).

Chimeric antibodies are those in which one or more regions of the antibody are from one species of animal and one or more regions of the antibody are from a different species of animal. A preferred chimeric antibody is one which includes regions from a primate immunoglobulin. A chimeric antibody for human clinical use is typically understood to have variable regions from a non-human animal, e.g. a rodent, with the constant regions from a human. In contrast, a humanized antibody uses CDRs from the non-human antibody with most or all of the variable framework regions from and all the constant regions from a human immunoglobulin. A human chimeric antibody is typically understood to have the variable regions from a rodent. A typical human chimeric antibody has human heavy constant regions and human light chain constant regions with the variable regions of both the heavy and light coming from a rodent antibody. A chimeric antibody may include some changes to a native amino acid sequence of the human constant regions and the native rodent variable region sequence. Chimeric and humanized antibodies may be prepared by methods well known in the art including CDR grafting approaches (see, e.g., U.S. Pat. Nos. 5,843,708; 6,180,370; 5,693,762; 5,585,089; 5,530,101), chain shuffling strategies (see e.g., U.S. Pat. No. 5,565,332; Rader et al. (1998)), molecular modeling strategies (U.S. Pat. No. 5,639,641), and the like.

A "humanized antibody" as used herein in the case of a two chain antibody is one where at least one chain is humanized. A humanized antibody chain has a variable region where one or more of the framework regions are human. A humanized antibody which is a single chain is one where the chain has a variable region where one or more of the framework regions are human. The non-human portions of the variable region of the humanized antibody chain or fragment thereof is derived from a non-human source, particularly a non-human antibody, typically of rodent origin. The non-human contribution to the humanized antibody is typically provided in form at least one CDR region which is interspersed among framework regions derived from one (or more) human immunoglobulin(s). In addition, framework support residues may be altered to preserve binding affinity.

The humanized antibody may further comprise constant regions (e.g., at least one constant region or portion thereof, in the case of a light chain, and preferably three constant regions in the case of a heavy chain). The constant regions of a humanized antibody if present generally are human. Methods to obtain "humanized antibodies" are well known to those skilled in the art. See, e.g., U.S. Patent Application Publication No. 2010/0080800.

The term constant region (CR) as used herein refers to constant regions genes of the immunoglobulin. The constant region genes encode the portion of the antibody molecule which confers effector functions. For Chimeric human antibodies and humanized antibodies, typically non-human (e.g., murine), constant regions are substituted by human constant regions. The constant regions of the subject chimeric or humanized antibodies are typically derived from human immunoglobulins. The heavy chain constant region can be selected from any of the five isotypes: alpha, delta, epsilon, gamma or mu. Further, heavy chains of various subclasses (such as the IgG subclasses of heavy chains) are responsible for different effector functions and thus, by choosing the desired heavy chain constant region, antibodies with desired effector function can be produced. Constant regions that may be used within the scope of this invention are gamma 1 (IgG1), particularly an Fc region of the gamma 1 (IgG1) isotype, gamma 3 (IgG3) and especially gamma 4 (IgG4). The light chain constant region can be of the kappa or lambda type, preferably of the kappa type. In one embodiment the light chain constant region is the human kappa constant chain (Hieter et al. (1980)) and the heavy constant chain is the human IgG4 constant chain.

The term variable region (VR) as used herein refers to the domains within each pair of light and heavy chains in an antibody that are involved directly in binding the antibody to the antigen. Each heavy chain has at one end a variable domain ($V_H$) followed by a number of constant domains. Each light chain has a variable domain ($V_L$) at one end and a constant domain at its other end; the constant domain of the light chain is aligned with the first constant domain of the heavy chain, and the light chain variable domain is aligned with the variable domain of the heavy chain.

The term framework region (FR) as used herein refers to one or more of the framework regions within the variable regions of the light and heavy chains of an antibody (See Kabat et al. (1992); Johnson and Wu (2001); http colon backslash backslash immuno dot bme dot nwa dot edu). These expressions include those amino acid sequences regions interposed between the CDRs within the variable regions of the light and heavy chains of an antibody.

CDR and FR residues are determined according to a standard sequence definition (Kabat et al. (1991), and a structural definition (e.g., as in Chothia and Lesk (1987)). Where these two methods result in slightly different identifications of a CDR, the structural definition is preferred, but the residues identified by the sequence definition method are considered important FR residues for determining which framework residues to import into a consensus sequence.

The term "monoclonal antibody" is also well recognized in the art and refers to an antibody that is the product of a single cloned antibody producing cell. Monoclonal antibodies are typically made by fusing a normally short-lived, antibody-producing B cell to a fast-growing cell, such as a cancer cell (sometimes referred to as an "immortal" cell). The resulting hybrid cell, or hybridoma, multiplies rapidly, creating a clone that produces the antibody.

The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')$_2$, Fabc and/or Fv fragments. The term "antigen-binding fragment" refers to a polypeptide fragment of an immunoglobulin or antibody that binds antigen or competes with intact antibody (i.e., with the intact antibody from which they were derived) for antigen binding (i.e., specific binding). Binding fragments are produced by recombinant DNA techniques, or by enzymatic or chemical cleavage of intact immunoglobulins. Binding fragments include Fab, Fab', F(ab').sub.2, Fabc, Fv, single chains, and single-chain antibodies.

Humanized antibody of reduced immunogenicity refers to a humanized antibody exhibiting reduced immunogenicity relative to the parent antibody, e.g., the murine antibody.

Humanized antibody substantially retaining the binding properties of the parent antibody refers to a humanized antibody which retains the ability to specifically bind the antigen recognized by the parent antibody, used to produce such humanized antibody. Preferably the humanized antibody will exhibit the same or substantially the same antigen-binding affinity and avidity as the parent antibody. Ideally, the affinity of the antibody will not be less than 10% of the parent antibody affinity, more preferably not less than about 30%, and most preferably the affinity will not be less than 50% of the parent antibody. Methods for assaying antigen-binding affinity are well known in the art and include half-maximal binding assays, competition assays, and Scatchard analysis.

Further, the term "therapeutically effective amount" refers to the amount of antibody which, when administered to a human or animal, which is sufficient to result in a therapeutic effect in said human or animal. The effective amount is readily determined by one of skill in the art following routine procedures.

As used herein, the terms "treat," "prevent," "preventing," and "prevention" refer to the prevention of the recurrence or onset of one or more symptoms of a disorder in a subject resulting from the administration of a prophylactic or therapeutic agent.

In a first aspect, the present invention provides monoclonal antibodies specific to a major neutralizing epitope of influenza H7 hemagglutinin and active fragments thereof, i.e., antigen binding fragments (also referred to herein as antibody fragments). In one embodiment, the monoclonal antibody or fragment thereof specifically binds to a conformational epitope of H7 hemagglutinin (HA), wherein the conformational epitope is comprised of amino acids 136Ser, 137Gly and 227Glu of the full length HA protein including the signal protein. The nucleotide sequence encoding the HA protein including signal protein is set forth in SEQ ID NO:1, and the amino acid sequence of the HA protein including signal protein is set forth in SEQ ID NO:2. In another embodiment, the monoclonal antibody or fragment thereof specifically binds to a conformational epitope of H7 hemagglutinin to which murine mAb 11B9 specifically binds. In an additional embodiment, the monoclonal antibody is murine mAb 11B9. In a further embodiment, the monoclonal antibody is murine mAb 11B9 produced by murine hybridoma 11B9. Murine hybridoma 11B9 was deposited on 11 Sep. 2012 under terms of the Budapest Treaty with CellBank. Australia; 214 Hawkesbury Rd, Westmead NSW 2145, Australia, and assigned Accession Number CBA20120022. The present invention also pertains to the murine hybridoma producing the murine monoclonal antibody 11B9. In another embodiment, the monoclonal antibody is a chimeric or humanized monoclonal antibody. In particular, the chimeric or humanized monoclonal antibody specifically binds to a conformational epitope of H5 hemagglutinin to which murine monoclonal antibody 11B9 specifically binds. In one embodiment, a monoclonal antibody (either a murine monoclonal antibody or a chimeric or humanized monoclonal antibody) or fragment thereof specifically binds to a conformational epitope of H7 hemagglutinin (HA), wherein the conformational epitope is comprised of amino acids 136Ser, 137Gly and 227Glu of the full length HA protein including the signal protein.

In one embodiment, the monoclonal antibody or fragment thereof specifically binds to a conformational epitope of H7 hemagglutinin (HA), wherein the conformational epitope is comprised of amino acids 175 Lys and 227Glu of the full length HA protein including the signal protein. The nucleotide sequence encoding the HA protein including signal protein is set forth in SEQ ID NO:1, and the amino acid sequence of the HA protein including signal protein is set forth in SEQ ID NO:2. In another embodiment, the monoclonal antibody or fragment thereof specifically binds to a conformational epitope of H7 hemagglutinin to which murine mAb 62 specifically binds. In an additional embodiment, the monoclonal antibody is murine mAb 62. In a further embodiment, the monoclonal antibody is murine mAb 62 produced by murine hybridoma 11B9. Murine hybridoma 62 was deposited on 11 Sep. 2012 under terms of the Budapest Treaty with CellBank Australia, 214 Hawkesbury Rd, Westmead NSW 2145, Australia, and assigned Accession Number CBA20120023. The present invention also pertains to the murine hybridoma producing the murine monoclonal antibody 62. In another embodiment, the monoclonal antibody is a chimeric or humanized monoclonal antibody. In particular, the chimeric or humanized monoclonal antibody specifically binds to a conformational epitope of H5 hemagglutinin to which murine monoclonal antibody 62 specifically binds. In one embodiment, a monoclonal antibody (either a murine monoclonal antibody or a chimeric or humanized monoclonal antibody) or fragment thereof specifically binds to a conformational epitope of H7 hemagglutinin (HA), wherein the conformational epitope is comprised of amino acids 175Lys and 227Glu of the full length HA protein including the signal protein.

In another embodiment, the present invention provides a nucleic acid encoding the murine mAb 11B9 or mAb 62 or chimeric or humanized monoclonal antibodies described herein or antigen binding fragment thereof. In an additional embodiment, the present invention provides a vector comprising the nucleic acid. In a further embodiment, the present invention proves a cell comprising and expressing the vector.

In one embodiment, humanized antibodies are prepared by combining human heavy and light chain constant regions with the mouse heavy and light chain variable regions using techniques described herein, as well as techniques well known to the skilled artisan. In another embodiment, humanized antibodies are prepared in which DNA sequences are synthesized which encode for humanized $V_L$ and $V_H$ sequences which contain the CDRs of the mouse light and heavy light chain variable regions of murine mAb 11B9 or mAb 62.

Methods for synthesizing DNA encoding for a protein of known sequence are well known in the art. Using such methods, DNA sequences which encode the subject humanized antibodies of the present invention are synthesized, and then expressed in vector systems suitable for expression of recombinant antibodies. This may be effected in any vector system which provides for the subject humanized antibody sequences of the present invention, such as expression of fusion proteins comprising the human constant domain sequences and the mouse variable domain sequences which are associated to produce functional (antigen binding) antibodies.

Expression vectors, host cells suitable for expression of recombinant antibodies and humanized antibodies in particular and methods suitable for expression of such antibodies are well known in the art. See, e.g., U.S. Pat. No. 7,074,406.

Host cells known to be capable of expressing functional immunoglobulins include by way of example mammalian cells such as Chinese Hamster Ovary (CHO) cells, COS cells, myeloma cells, bacteria such as *Escherichia coli*, yeast cells such as *Saccharomyces cerevisiae*, among other host cells. Of these, CHO cells are used by many researchers given their ability to effectively express and secrete immunoglobulins.

Essentially, recombinant expression of humanized antibodies is effected by one of two general methods. In the first method, the host cells are transfected with a single vector which provides for the expression of both heavy and light variable sequences fused to selected constant regions. In the second method, host cells are transfected with two vectors, which respectively provide for expression of either the variable heavy or light sequence fused to selected constant regions.

In a second aspect, the present invention provides methods and compositions for the prophylaxis and treatment of H7 influenza using a monoclonal antibody or antibody fragment described herein, such as a murine mAb 11B9 or mAb 62 or chimeric or humanized monoclonal antibodies or fragments thereof. In one embodiment, the present invention provides a pharmaceutical composition comprising the murine mAb 11B9 or mAb 62 or the chimeric or humanized monoclonal antibodies described herein and a pharmaceutically acceptable diluent or carrier. In another embodiment, the pharmaceutical composition comprises an antigen binding fragment of the monoclonal antibodies described herein and a pharmaceutically acceptable diluent or carrier. In one embodiment, the antigen binding fragment is an antigen binding fragment of mAb 11B9 or mAb 62. In an additional embodiment, the pharmaceutical composition comprises a nucleic acid molecule encoding said antibody or antibody fragment and a pharmaceutically acceptable diluent or carrier. In a further embodiment, the pharmaceutical composition comprises a vector comprising said nucleic acid and a pharmaceutically acceptable diluent or carrier. In another embodiment, the pharmaceutical composition comprises a cell expressing said vector and a pharmaceutically acceptable diluent or carrier.

In one embodiment, the present invention provides a method of reducing influenza H5N1 virus infection in a subject, or lowering the risk of influenza H7 virus infection in a subject, inhibiting infection of a subject by one or more influenza H7 virus strains or isolates, or prophylaxis of influenza infection or disease by one or more influenza H7 virus strains or isolates. In this embodiment, the method comprises administering to a subject in need thereof, a therapeutically effective amount of a monoclonal antibody described herein such as the murine mAb 11B9 or mAb 62 or the chimeric or humanized monoclonal antibodies described herein, or an antigen binding fragment thereof, a nucleic acid molecule comprising a polynucleotide encoding said antibody or antibody fragment; a vector comprising said polynucleotide; or a cell expressing said vector. In one embodiment, the subject is immunocompromised, is an infant, is a young child or is elderly. In another embodiment, administration provides a therapeutic benefit. In an additional embodiment, therapeutic benefit comprises inhibiting increases in influenza virus titer, decreasing influenza virus titer, inhibiting increases in influenza virus replication, decreasing influenza virus replication, inhibiting increases in influenza virus proliferation or decreasing influenza virus proliferation, or decreasing progression, severity, frequency, duration or probability one or more symptoms or complications associated with influenza virus infection in a subject. In one embodiment, a symptom or complication is selected from chills, fever, cough, sore throat, nasal congestion, sinus congestion, nasal infection, sinus infection, body ache, head ache, fatigue, pneumonia, bronchitis, ear infection, ear ache and death. In another embodiment, the therapeutic benefit comprises hastening a subject's recovery from influenza H7 virus infection. In a further embodiment, the agent that is administered to the subject is administered prior to, substantially contemporaneously with or following influenza H7 virus infection of the subject.

The antibodies according to the invention can be prepared in a physiologically acceptable formulation and may comprise a pharmaceutically acceptable carrier, diluent and/or excipient using known techniques. For example, the antibody according to the invention and as described herein including any functionally equivalent antibody or functional parts thereof is combined with a pharmaceutically acceptable carrier, diluent and/or excipient to form a therapeutic composition. Suitable pharmaceutical carriers, diluents and/or excipients are well known in the art and include, for example, phosphate buffered saline solutions, water, emulsions such as oil/water emulsions, various types of wetting agents, sterile solutions, etc.

Formulation of the pharmaceutical composition according to the invention can be accomplished according to standard methodology know to those skilled in the art. See, e.g., *Remington: The Science and Practice of Pharmacy,* 21st Ed., Ed. D. B. Troy, Lippincott, Williams & Wilkins, Baltimore, 2006, hereby incorporated by reference herein.

The compositions of the present invention may be administered to a subject in the form of a solid, liquid or aerosol at a suitable, pharmaceutically effective dose. Examples of solid compositions include pills, creams, and implantable dosage units. Pills may be administered orally. Therapeutic creams may be administered topically. Implantable dosage units may be administered locally, for example, at a tumor site, or may be implanted for systematic release of the therapeutic composition, for example, subcutaneously. Examples of liquid compositions include formulations adapted for injection intramuscularly, subcutaneously, intravenously, intra-arterially, and formulations for topical and intraocular administration. Examples of aerosol formulations include inhaler formulations for administration to the lungs.

The compositions may be administered by standard routes of administration. In general, the composition may be administered by topical, oral, rectal, nasal, interdermal, intraperitoneal, or parenteral (for example, intravenous, subcutaneous, or intramuscular) routes. In addition, the composition may be incorporated into sustained release matrices such as biodegradable polymers, the polymers being implanted in the vicinity of where delivery is desired, for example, at the site of a tumor. The method includes administration of a single dose, administration of repeated doses at predetermined time intervals, and sustained administration for a predetermined period of time. A sustained release matrix, as used herein, is a matrix made of materials, usually polymers which are degradable by enzymatic or acid/base hydrolysis or by dissolution. Once inserted into the body, the matrix is acted upon by enzymes and body fluids. The sustained release matrix desirably is chosen by biocompatible materials such as liposomes, polylactides (polylactide acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

The composition may be administered in combination with other compositions comprising an biologically active substance or compound, particularly at least one compound selected from the group consisting of compounds against oxidative stress, anti-apoptotic compounds, metal chelators, inhibitors of DNA repair such as pirenzepin and metabolites, 3-amino-1-propanesulfonic acid (3APS), 1,3-propanedisulfonate (1,3PDS), α-secretase activators, β- and γ-secretase inhibitors, tau proteins, neurotransmitter, β-sheet breakers, attractants for amyloid beta clearing/depleting cellular components, inhibitors of N-terminal truncated amyloid beta including pyroglutamated amyloid beta 3-42, anti-inflammatory molecules, "atypical antipsychotics" such as, for example clozapine, ziprasidone, risperidone, aripiprazole or olanzapine or cholinesterase inhibitors (ChEIs) such as tacrine, rivastigmine, donepezil, and/or galantamine, M1 agonists and other drugs including any amyloid or tau modifying drug and nutritive supplements such as, for example, vitamin B12, cysteine, a precursor of acetylcholine, lecithin, choline, *Ginkgo biloba*, acetyl-L-carnitine, idebenone, propentofylline, or a xanthine derivative, together with an antibody according to the present invention and, optionally, a pharmaceutically acceptable carrier and/or a diluent and/or an excipient and procedures for the treatment of diseases.

Proteinaceous pharmaceutically active matter may be present in amounts between 1 ng and 10 mg per dose. Generally, the regime of administration should be in the range of between 0.1 μg and 10 mg of the antibody according to the invention, particularly in a range 1.0 μg to 1.0 mg, and more particularly in a range of between 1.0 μg and 100 μg, with all individual numbers falling within these ranges also being part of the invention. If the administration occurs through continuous infusion a more proper dosage may be in the range of between 0.01 μg and 10 mg units per kilogram of body weight per hour with an individual numbers falling within these ranges also being part of the invention.

Administration will generally be parenterally, e.g., intravenously. Preparations for parenteral administration include sterile aqueous or non-aqueous solutions, suspensions and emulsions. Non-aqueous solvents include without being limited to it, propylene glycol, polyethylene glycol, vegetable oil such as olive oil, and injectable organic esters such as ethyl oleate. Aqueous solvents may be chosen from the group consisting of water, alcohol/aqueous solutions, emulsions or suspensions including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose) and others. Preservatives may also be present such as, for example, antimicrobials, antioxidants, chelating agents, inert gases, etc.

The pharmaceutical composition may further comprise proteinaceous carriers such as, for example, serum albumin or immunoglobulin, particularly of human origin. Further biologically active agents may be present in the pharmaceutical composition of the invention dependent on the intended use.

In a third aspect, the present invention provides methods and compositions for the identification, characterization and quantification of H7 expression using a monoclonal antibody or fragments thereof described herein. In some embodiments, the monoclonal antibody is murine mAb 11B9 or mAb 62. In one embodiment, the H5 expression relates to the expression of HA of H7 influenza viruses. In one embodiment, the composition comprises a monoclonal antibody or fragments thereof described herein. In some embodiments, the monoclonal antibody is murine mAb 11B9 or mAb 62. In another embodiment, the method comprises detecting the binding of the H5 with a monoclonal antibody or fragments thereof described herein. In some embodiments, the monoclonal antibody is murine mAb 11B9 or mAb 62. In one embodiment, the invention relates to immunofluorescence assays (IFA), immunohistochemical assays and other methods that utilize such monoclonal antibodies or related binding proteins, including ELISA, hemagglutination inhibition (HI) assays and virus neutralization (VN) assays. All of these assays are well known to the skilled artisan. In one embodiment, a dual function ELISA as described herein can be utilized.

In some embodiments, the methods and compositions for the identification and/or quantification of H7 expression are for the identification and/or quantification of an immunogenic agent of an H7 virus in a vaccine 8. In one embodiment, the immunogenic agent comprises a hemagglutinin or antigenic portion thereof or a nucleic acid encoding the hemagglutinin or antigenic portion thereof. In another embodiment, the antigenic portion includes an epitope of hemagglutinin. In one embodiment, the immunogenic agent is a virus comprising hemagglutinin. In another embodiment, the virus is inactivated. In an additional embodiment, the virus is an attenuated virus. In another embodiment, the virus is in the form of a virosome. In a further embodiment, the virus is egg-derived or cell culture-derived. In another embodiment, the immunogenic agent is a split virus comprising hemagglutinin or a split virus antigenic preparation. In one embodiment, the immunogenic agent is hemagglutinin or antigenic portion thereof. In another embodiment, the hemagglutinin or antigenic portion thereof has been isolated. In an additional embodiment, the hemagglutinin or antigenic portion thereof is produced by an expression system. In one embodiment, the expression system is any expression system, such as a viral expression vector in which the hemagglutinin or antigenic portion thereof is presented or displayed on the surface of the virus. In one embodiment, the viral expression vector is any viral expression vector such as a modified vaccinia virus expression vector, an adenovirus expression vector, a poxvirus expression vector, a baculovirus expression vector and the like. In one embodiment, the expression vector is a baculovirus expression vector and the virus presenting or displaying the hemagglutinin or antigenic portion thereof is a baculovirus. In another embodiment, the immunogenic agent is a nucleic acid encoding the hemagglutinin or antigenic portion thereof which is capable of expression in the subject.

In a fourth aspect, the present invention provides kits and methods for the detection of an influenza A H7 subtype virus in a biological specimen or for the detection of an antibody to an influenza A H7 hemagglutinin (referred to herein as an anti-H7 antibody) in a biological specimen. In one embodiment for the detection of an influenza A H7 subtype virus in a biological specimen, the method comprises contacting the specimen with a first antibody which is a monoclonal antibody or antibody fragment thereof as described herein (sometimes referred to as a capture antibody). In another embodiment, the method further comprises contacting the specimen with a second antibody or antibody fragment thereof as described herein that specifically binds to an epitope of H7 hemagglutinin of an influenza A H7 subtype virus in which the second antibody contains or is conjugated to a detectable element (sometimes referred to as a detector antibody). In one embodiment for the detection of an antibody to an influenza A H7 hemagglutinin in a biological specimen, the method comprises contacting the specimen to which a control H7 hemagglutinin of an influenza A H7 subtype virus (sometimes referred to herein as a control H7 antigen) has been added with a first antibody which is a monoclonal antibody or antibody fragment thereof as described herein (sometimes referred to as a capture antibody). In another embodiment, the method further comprises contacting the specimen with a second antibody or antibody fragment thereof as described herein that specifically binds to an epitope of H7 hemagglutinin of an influenza A H7 subtype virus in which the second antibody contains or is conjugated to a detectable element (sometimes referred to as a detector antibody). In some embodiments, the second antibody contains a radioactive atom, is conjugated to a fluorescent molecule, or is conjugated to an enzyme. In other embodiments, the first antibody is immobilized on a solid surface. In some embodiments, the first monoclonal antibody is murine mAb 11B9 or mAb 62. In other embodiments, the second monoclonal antibody is mAb 11B9 or mAb 62. In one embodiment, the control H7 antigen is a recombinant H7 antigen. In another embodiment, the control H7 antigen is a H7 surface expressing virus, such as a baculovirus. In one embodiment, the invention relates to immunofluorescence assays (IFA), immunohistochemical assays and other methods that utilize such monoclonal antibodies or related binding proteins, including ELISA, hemagglutination inhibition (HI) assays and virus neutralization (VN) assays. In one embodiment, a dual function ELISA assay as described herein is utilized.

In one embodiment, the assay is a dual function ELISA that is effective for both antigen and antibody detection of H7 avian influenza virus. In one embodiment, one of mAb 11B9 or mAb 62 is used as the capture antibody and the other of mAb 11B9 or mAb 62 is used as the detector antibody. In one embodiment, the capture antibody is coated on a solid phase, such as a microtiter plate, a microbead, or the like. To detect antigen in a biological sample, the sample is contacted with the capture antibody for a period of time sufficient to allow any H7 antigens in the sample to bind to the capture antibody. The detector antibody is then contacted with the bound sample H7 antigens, if any, for a period of time sufficient to allow the dectector antibody to bind to the bound sample H7 antigens. The binding of any detector antibody is then determined in order to determine the presence and/or the amount of H7 antigens in the sample. To detect anti-H7 antibody in a biological sample, a control H7 antigen is added to a biological sample to prepare a mixture. In one embodiment, a fixed amount of the control H7 antigen is added to the biological sample. The control H7 antigen binds to any anti-H7 antibody that may be present in the biological sample. The mixture is then contacted with the capture antibody for a period of time sufficient to allow the control H7 antigen to bind to the capture antibody. If anti-H7 antibodies are present in the biological, some of the control H7 antigen bound to the capture antibody will be bound to anti-H7 antibodies and some of the control H7 antigen bound to the capture antibody will be free from bound antibodies. In one embodiment, the control H7 antigen is a recombinant H7 antigen. In another embodiment, the control H7 antigen is a H7 surface expressing virus, such as a baculovirus. The detector antibody is then contacted with any bound control H7 antigen not bound by sample H7 antibodies, if any, for a period of time sufficient to allow the dectector antibody to bind to the bound control H7 antigen not bound by sample H7 antibodies. The binding of detector antibody is then determined in order to determine the presence and/or the amount of H7 antibodies in the sample. In one embodiment, a reduced level of bound detector antibody is indicative of the presence of anti-H7 antibodies in the biological sample.

In one embodiment, the kit comprises a first antibody which is a monoclonal antibody or antibody fragment thereof described herein together with instructions for performing an assay to detect the influenza A H7 subtype virus. In some embodiments, the monoclonal antibody is murine mAb 11B9 or mAb 62. In another embodiment, the kit further comprises a second antibody that specifically binds to an epitope of H7 hemagglutinin of an influenza A virus in which the second antibody contains or is conjugated to a detectable element. In some embodiments, the second antibody is mAb 11B9 or mAb 62. In some embodiments, the second antibody contains a radioactive atom, is conjugated to a fluorescent molecule, or is conjugated to an enzyme. In other embodiments, the first antibody is immobilized on a solid surface. In another embodiment, the kit further comprises an H7 hemagglutinin antigen. In some embodiments, the H7 hemagglutinin antigen is a recombinant H7 protein. In other embodiments, the H7 hemagglutinin antigen is a H7 surface expressing virus, such as a baculovirus. In one embodiment, the kits are useful for identifying and/or quantifying an immunogenic agent of an H7 virus in a vaccine. In another embodiment, the kits are useful for detecting an H7 hemagglutinin or an antibody against an H7 hemagglutinin in a biological sample. In some embodiments, the kits relate to immunofluorescence assays (IFA), immunohistochemical assays and other methods that utilize such binding proteins, including ELISA, hemagglutination inhibition (HI) assays and virus neutralization (VN) assays. All of these assays are well known to the skilled artisan. In some embodiments, a dual function ELISA such as described herein can be utilized.

In the present study, a panel of mAbs against H7 HA1 was characterized and their respective neutralizing epitopes were identified. The prophylactic efficacies of these mAbs were evaluated in mice challenged with HPAI H7N7 virus infection. Efficacy was determined by observation of weight loss, survival and kinetics of viral load clearance in the lungs of the infected mice.

As shown herein, mAb 11B9 and mAb 62, generated from 117N1 immunized mice, are able to specifically react and neutralize different H7 influenza virus strains. Based on their neutralizing activity, the neutralizing epitopes of the two mAbs were identified with escape mutant sequencing. Passive administration of antibodies remains a strategy against pandemic influenza. Therefore, the prophylatic efficacy of the two mAbs against H7 influenza virus was evaluated in mice in terms of percent survival and percent body weight. Administration of either mAb 11B9 or mAb 62 in a single dose showed 100% protection against lethal H7N7 influenza in a mouse model. Therapy with these two mAbs helped to control the initial course of infection, thus allowing the animal to mount an effective immune response. These studies show that passive immunotherapy using either mAb 11B9 or mAb 62 is an effective tool in the prophylaxis of highly pathogenic H7N7 infection, providing the immediate immunity needed to contain a future influenza pandemic. The clinical application of this approach is further ascertained by humanization of these antibodies and evaluation as therapeutic agents in nonhuman primates challenged with influenza H7N7 viruses.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Green and Sambrook, 2012, *Molecular Cloning*, 4th Ed. (Cold Spring Harbor Laboratory Press, Cold Spring Harbor, N.Y.); Ausubel et al., 1992, *Current Protocols in Molecular Biology* (John Wiley & Sons, including periodic updates); Glover, 1985, *DNA Cloning* (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, *Antibodies*, (Cold Spring Harbor Laboratory Press, Cold Spring Harbor, N.Y.); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Fire et al., *RNA Interference Technology: From Basic Science to Drug Development*, Cambridge University Press, Cambridge, 2005; Schepers, *RNA Interference in Practice*, Wiley-VCH, 2005; Engelke, *RNA Interference (RNAi): The Nuts & Bolts of siRNA Technology*, DNA Press, 2003; Gott, *RNA Interference, Editing, and Modification: Methods and Protocols (Methods in Molecular Biology)*, Human Press, Totowa, N.J., 2004; Sohail, *Gene Silencing by RNA Interference: Technology and Application*, CRC, 2004.

EXAMPLES

The present invention is described by reference to the following Examples, which is offered by way of illustration and is not intended to limit the invention in any manner.

Standard techniques well known in the art or the techniques specifically described below were utilized.

Example 1

Materials and Methods

Viruses and cells: H7N1 (A/chicken/Malaysia/94) and the other AIV used in this study were obtained from Agri-Food & Veterinary Authority of Singapore. Reassortant influenza virus H7N9 (A/Shanghai/1/13), H7N3 (A/Canada/rv504/04), H7N6 (A/quail/Aichi/3/09), H7N7 (A/duck/Hokkaido/1/10) and H7N7 (A/Netherlands/219/03) were generated by reverse genetics as described previously (Ho et al., 2009). Briefly, the complementary DNA of the HA and NA genes of H7 viruses were synthesized based on the sequences from the NCBI influenza database while the six cDNAs of the internal genes were synthesized based on the PR8 (A/Puerto Rico/8/1934) virus sequence (GenScript, USA). The cDNA of each of the eight influenza virus gene segments was inserted between the pol I promoter (plh) and the pol I terminator of pClpolsapIT vector (kindly provided by Ruben Donis, CDC, USA) and cotransfected into cocultured 293T human embryonic kidney (293T) cells and Madin-Darby canine kidney (MDCK) cells using lipofectamine 2000 (Life Technologies, USA). After 48 h the transfected supernatants were collected and virus titers were determined by standard hemagglutination assays. The sequences were confirmed using a specific set of universal primers as described previously (Prabakaran et al., 2009). Stock viruses were propagated in the allantoic cavities of 11-day-old embryonated chicken eggs at 35° C. for 36 h-91 h. The tissue culture infectious dose 50 (TCID50) of reassortant virus was then calculated by the Muench-Reed method (1938).

MDCK cells were obtained from the American Type Culture Collection (ATCC). MDCK cells were propagated in Dulbecco's minimal essential medium (DMEM; Life Technologies, USA) supplemented with 10% fetal bovine serum. Virus stocks were grown in MDCK cells in DMEM supplemented with 0.5% bovine serum albumin (BSA) and 200 ng/ml of trypsin. 293T cells were maintained in Opti-MEMI (Life Technologies, USA) containing 5% FBS.

All experiments with highly pathogenic viruses were conducted in a biosafety level 3 (BSL 3) containment facility in compliance with CDC/NIH and WHO recommendations and also were approved by the Agri-Food and Veterinary Authority of Singapore.

MAb production: BALB/c mice were immunized twice subcutaneously at regular intervals of 2 weeks with binary ethylenimine (BEI) inactivated whole virus from H7N1 (A/chicken/Malaysia/94) in 0.1 ml of Phosphate Buffered Saline (PBS), which was emulsified with an equal volume of Montanide ISA 563 adjuvant (SEPPIC, France). Mice were boosted with the same viral antigen, 3 days before the fusion of splenocytes with SP2/0 cells (He et al., 2009). The fused cells were seeded in 96-well plates, and their supernatants were screened by immunofluorescence assays as described below. The hybridomas that produced the mAbs were cloned by limiting dilution at least three times. The positive mAbs were tested for their hemagglutination inhibition activity as described below. Immunoglobulins from selected positive mAbs were isotyped using a commercial isotyping kit (Amersham Bioscience, England) as described in the manufacturer's protocol. The hybridoma suspension was harvested 3 days postseeding and cell debris pelleted by centrifugation at 400 g for 10 min, followed by collection of the supernatant and storage at −20° C. The mAbs were purified with Montage kit Prosep-G (Millipore) for IgG or were purified using Protein A sepharose beads (Millipore). Purity of the antibodies was confirmed by SDS-PAGE analysis. The mAbs were then tested for neutralization activity by standard hemagglutination inhibition assay as described below.

Immunofluorescence assay (IFA): MDCK cells cultured in 96-well plates were infected with different AIV H7 strains. At 24 h post-infection, the cells were fixed with 4% paraformaldehyde for 30 min at room temperature and washed thrice with phosphate buffered saline (PBS), pH 7.4. Fixed cells were incubated with hybridoma culture supernatant at 37° C. for 1 h, rinsed with phosphate buffered saline (PBS) and then incubated with a 1:400 or a 1:200 dilution of fluorescein isothiocyanate (FITC)-conjugated rabbit anti-mouse Immunoglobulin (Dako, Denmark). Cells were rinsed again in PBS and antibody binding was evaluated by wide-field epi-fluorescence microscopy (Olympus IX71).

Hemagglutination inhibition assay: Hemagglutination inhibition (HI) assays were performed as described previously ((Prabhu et al., 2009; Prabakaran et al., 2010). Briefly, mAbs were serially diluted (2 fold) in V-bottom 96-well plates and mixed with 4 HA units of H7 virus. Plates were incubated for 30 min at room temperature, and 1% chicken RBCs were added to each well. The hemagglutination inhibition endpoint was the highest mAb dilution in which agglutination was not observed.

Microneutralization assay: Neutralization activity of the monoclonal antibody against H7 strains was analyzed by microneutralization assays as previously described (He and Kwang, 2013). Briefly, ten times diluted mAb was further serially diluted (two-fold) and incubated with 100 50% tissue culture infectious doses (TCID50) of different clades of H7 strains for 1 h at room temperature and plated in duplicate onto MDCK cells grown in a 96-well plate. Alternatively, the mAb was serially two-fold diluted and incubated with 100 TCID50 of different clades of H7 strains for 1 h at room temperature and plated in duplicate onto MDCK cells grown in a 96-well plate. The TCID50 of each of the H7 strains in MDCK cell culture was determined by the Reed and Muench (1938) method. The neutralizing titer was assessed as the highest mAb dilution in which no cytopathic effect was observed by light microscopy.

Isolation and analysis of escape mutants: The epitope recognized by mAb 11B9 and mAb 62 were mapped by characterization of escape mutants as described previously (He et al., 2010; Kaverin et al., 2007). Briefly, H7 parental viruses were incubated with an excess of mAb for 1 h and then inoculated into 11 day old embryonated chicken eggs. The eggs were incubated at 37° C. for 48 h-72 h. Virus was harvested and used for cloning in limiting dilution in embryonated chicken eggs and the escape mutants were plaque purified. RNA was extracted from the allantoic fluid. The hemagglutinin (HA) gene was reverse transcriptase (RT)-PCR amplified and cloned into a TA-cloning vector (Promega) and several clones were sequenced. The sequences of individual clones were analyzed by comparison with the sequences of the parental virus.

Challenge study (Example 4): Inbred SPF BALB/c mice aged 4-6 weeks were used for the challenge studies. Mice (n=10 per group) were intranasally infected with 5MLD50 (Mouse lethal dose 50%) of adapted H7N7 strains (A/Netherlands/219/03). All animal experiments were carried out in accordance with the Guides for Animal Experiments Performed at NIID and experimental protocols.

Prophylactic efficacy (Example 4): To determine the prophylactic efficacy, mice were pre-treated intraperitoneally with 10 mg/kg or 0 mg/kg (PBS) of either mAb 11B9 or mAb 62, prior to the viral challenge. After 24 h, mice were challenged with 5MLD50 of the H7N7 strain. Mice were observed daily to monitor body weight and mortality until all animals died or until day 14 after challenge.

Immunization and challenge (Examples 6-10): For challenge experiments H7N7 reassortant virus was mouse adapted by three sequential lung to lung passages, as described previously (Brown, 1990). Virus present in the lung passage was propagated in the allantoic cavities of 10 days old chicken eggs for 48 h at 37° C. to prepare a virus stock. 50% mouse lethal dose (MLD50) was calculated as described by Reed and Munch method. Groups of SPF female BALB/c mice aged 4-6 weeks were used for the challenge studies. Mice (n=5 per group) were inoculated intranasally with 5 or 10 MLD50 (Mouse lethal dose 50%) of pathogenic H7N7 (A/Netherlands/219/03) strain.

For intranasal immunization, mice were first anesthetized intraperitoneally with 100 ul of saline with ketamine (10 mg/ml) and xylazine (1 mg/ml). Each mouse was inoculated intranasally with 100 ul of Mab or virus in PBS.

Prophylactic efficacy (Examples 6-10): To determine the prophylactic efficacy, mice were pre-treated intranasally or intraperitoneally with 2.5 mg/kg, 5 mg/kg or 10 mg/kg of purified Mab 62, prior to the viral challenge. Control mice were treated intranasally with PBS only. After 24 h, mice were challenged with 5 MLD50 of the H7N7 strain. Mice were observed daily to monitor body weight and mortality until death or day 14 after challenge.

Therapeutic efficacy (Examples 6-10): To determine the therapeutic efficacy, each group of mice was experimentally infected with 5 MLD50 of the H7N7 strain. One day, two days or seven days after viral infection, the mice groups were treated either via intranasal or intraperitoneal route with 5 mg/kg, 10 mg/kg or 15 mg/kg of Mab 62. Infected control mice were treated intranasally with PBS only. Mice were observed daily to monitor body weight and mortality until death or day 14 after challenge.

Histophathological analysis (Examples 6-10): Lung samples for histological examination were harvested from each mice group (N=3) on day 2, day 4 and day 6 post-challenge and fixed in 10% buffered formalin (pH 7.4), embedded in paraffin and sectioned at 4 urn. The sections were deparaffinized using Hist-choice (Amersco) and rehydrated in sequentially graduated ethanol baths. The slides were stained with hematoxylin and eosin and pathological evaluation was performed by light microscope (Olympus, UK). The images were captured by digital imaging system (Nikon, USA).

Statistical analysis (Examples 6-10): The data are expressed as arithmetic means and standard deviations (SD). An unpaired two-tailed Student's t test was performed to determine the level of significance in the difference between the means of two groups. One-way analysis of variance (ANOVA) was also used to test for differences between groups. All statistical analyses were done with SigmaStat 2.0 (Jandel Corporation) software.

Experimental serum samples Examples 11-15): Inactivated AI viruses (Table 1) were emulsified in ISA-70 (SEPPIC, France) adjuvant and injected intramuscularly to the groups of three weeks old white leghorn chickens (n=4). The booster was given twice at two-week intervals. Sera were prepared from the blood collected 10 days after 1st injection and $2^{nd}$ injection. Antibody responses to the homologous strains were evaluated by HI as described below. Groups of mice (n=4) were injected intramuscularly with different inactivated H7 AIVs individually emulsified in adjuvant (SEPPIC, France). The injections were repeated twice at two-week intervals. In addition, guinea pigs were immunized with inactivated H7N1 (A/Chicken/Malaysia/94). Blood was collected 14 days after the 2nd immunization.

H7 baculovirus production (Examples 11-15): The recombinant baculovirus vector was generated as described previously (Prabakaran et al., 2010). The full length HA gene was amplified from H7N7 (A/NL/219/03) reassortant virus in a standard PCR reaction. The amplified HA gene was inserted into the shuttle vector pFASTBacHT A (Invitrogen, San Diego, Calif., USA) for expression under the white spot syndrome virus (WSSV) immediate early (iel) promotor. This expression cassette was integrated into the baculovirus genome within DH10Bac™ (Invitrogen, USA) through site specific transposition according to the protocol of the Bac-to-Bac system (Invitrogen). SF9II cells were maintained in SF900II serum free medium (Gibco BRL, USA) at 28° C. for recombinant baculovirus synthesis. The recombinant bacmid was then transfected into SF9II cells and the supernatant containing recombinant baculovirus displayed H7-HA (Bac-H7) was harvested at 96 h post-infection.

Dual function ELISA (Examples 11-15): 96-well, round-bottom microtiter plates (Nunc, Roskilde, Demark) were coated with 0.5 µg/well of capture mAb 11B9 in 100 µl of carbonate buffer (73 mM sodium bicarbonate and 30 mM sodium carbonate, pH 9.7) overnight at 4° C. or 37° C. for 2 h. The plates were washed twice with PBST, followed by two washes with PBS after each incubation with antibody or antigen. The antibody-coated plates were blocked by incubation with 100 µl of blocking buffer (PBS containing 5% milk) for 1 h at room temperature. For antigen detection, the blocked plates were then incubated at 37° C. for 1 h with 100 µl of virus-containing samples diluted in PBST. For antibody detection, 50 µl of serum samples mixed with 50 µl of H7 surface expressing baculovirus of 8 HAU were added to the blocked plates for 1-hour-incubation at 37° C. Virus binding or antibody blocking was detected by incubation for 1 h at 37° C. with 100 µl of horseradish peroxidase-conjugated detection mAb 62 (800 ng) (in-house labeling; Roche). Chromogen development was mediated by the addition of 100 µl of freshly prepared substrate solution (o-phenylenediamine-dihydrochloride; Sigma). The reaction was stopped with sulfuric acid of 0.1 N, and the optical density at 490 nm was recorded. The antigen detection limit was determined by the optical density value that gave a signal-to-noise ratio of 3. For antibody detection, the OD intensity reduction caused by serum antibodies blocking mAb binding was calculated for each sample dilution by using the formula: % inhibition= [(negative reference serum OD−test serum OD)/(negative reference serum OD−positive reference serum OD)]×100%. To determine the cut-off value of antibody detection, specific pathogen-free chicken sera, mice and guinea pigs were obtained from the Animal Health Biotechnology Serum Bank, Temasek Life Sciences Laboratory, Singapore.

Example 2

Characterization of Murine Monoclonal Antibodies 11B9 and 62

Monoclonal antibodies 11B9 and 62 were produced from mice immunized with A/chicken/Malaysia/94 H7N1 virus. Both mAb 11B9 and mAb 62 were identified as belonging to isotype IgG1. All of the present neutralizing activity against H7N1 strain A/chicken/Malaysia/94, besides positive activity in IFA with H7N1 infected MDCK cells (FIGS. 1A and 1B), suggested that they both recognize neutralizing epitopes in H7. The two mAbs were further tested against different H7 strains in neutralization and IFA. In IFA with different AIV infected MDCK cells, both two mAbs presented specific reaction with all the four H7 strains tested without any cross reaction with any non-H7 AIV strains. (Table 1): Thus, mAb 11B9 and mAb 62 are specific to H7 subtypes without any interaction to non-H7 strains. The similar result was observed in neutralization test with different AIVs. mAb 11B9 and mAb 62 are able to neutralize all four H7 tested while no activity was detected with any non-H7 strains (Table 2), indicating both mAbs are H7 specific neutralizing antibodies.

TABLE 1

Monoclonal Antibodies 11B9 and 62
Screened in Various AIV Infected MDCK Cells

| Virus | mAb 62 | mAb 11B9 | PBS |
|---|---|---|---|
| A/chicken/Singapore/94 (H7N1) | + | + | − |
| A/Netherlands/219/03 (H7N7) | + | + | − |
| A/duck/Hokkaido/1/10(H7N7) | + | + | − |
| A/Canada/rv504/04 (H7N3) | + | + | − |
| A/Chicken/Malaysia/04 (H5N2) | − | − | − |
| A/chicken/Singapore/02 (H3N2) | − | − | − |
| A/Singapore/TLL54/2009 (H1N1) | − | − | − |
| A/Chicken/Singapore/Singapore/98 (H9N2) | − | − | − |
| A/Chicken/Singapore/Singapore/92 (H4N1) | − | − | − |
| Uninfected MDCK | − | − | − |

TABLE 2

Neutralization titer with Mab 11B9 and 62[a,b]

| Virus | mAb 62 | mAb 11B9 | PBS |
|---|---|---|---|
| A/chicken/Singapore/94 (H7N1) | 256 | 256 | <8 |
| A/Netherlands/219/03 (H7N7) | 256 | 256 | <8 |
| A/duck/Hokkaido/1/10 (H7N7) | 256 | 64 | <8 |
| A/Canada/rv504/04 (H7N3) | 32 | 128 | <8 |
| A/Chicken/Malaysia/04 (H5N2) | <8 | <8 | <8 |
| A/chicken/Singapore/02 (H3N2) | <8 | <8 | <8 |
| A/Singapore/TLL54/2009 (H1N1) | <8 | <8 | <8 |
| A/Chicken/Singapore/Singapore/98 (H9N2) | <8 | <8 | <8 |
| A/Chicken/Singapore/Singapore/92 (H4N1) | <8 | <8 | <8 |

[a]Concentration of MAb at 0.1 mg/ml.
[b]One hundred TCID50 of each virus strain used for microneutralization assays.

Example 3

Epitope Mapping for Murine Monoclonal Antibodies 11B9 and 62

Since the two mAbs are able to neutralize H7 viruses, the amino acids involved in forming the epitopes of the two mAbs were analyzed using selection of neutralization escape mutants. A/chicken/Malaysia/94 H7N1 virus was used as parental virus for the selection. Sequences of the complete HA genes isolated from multiple escape variants were compared with the parental virus. It was found that mutants from mAb 11B9 carried double mutations either at amino acid combination 136 (Ser to Gly) and 227 (Glu to Gly), or 137 (Gly to Arg) and 227 (Glu to Gly), while mutants with mAb 62 have double mutations on amino acids 175 (Lys to Glu) and 227(Glu to Gly). Sequence numbers include signal peptide (Table 3).

TABLE 3

Neutralizing Epitopes of H7 HA using
mAb 11B9 and mAb 62 by Escape Mutations

| mAb | Nucleotide | Nucleotide Change | Amino Acid | Amino acid Change |
|---|---|---|---|---|
| 11B9 | 406 | A to G | 136 | Ser to Gly |
|  | 680 | A to G | 227 | Glu to Gly |
|  | 407 | G to A | 136 | Ser to Asn |
|  | 680 | A to G | 227 | Glu to Gly |
|  | 409 | G to A | 137 | Gly to Arg |
|  | 680 | A to G | 227 | Glu to Gly |
| 62 | 523 | A to G | 175 | Lys to Glu |
|  | 680 | A to G | 227 | Glu to Gly |

Example 4

Figure 1B:
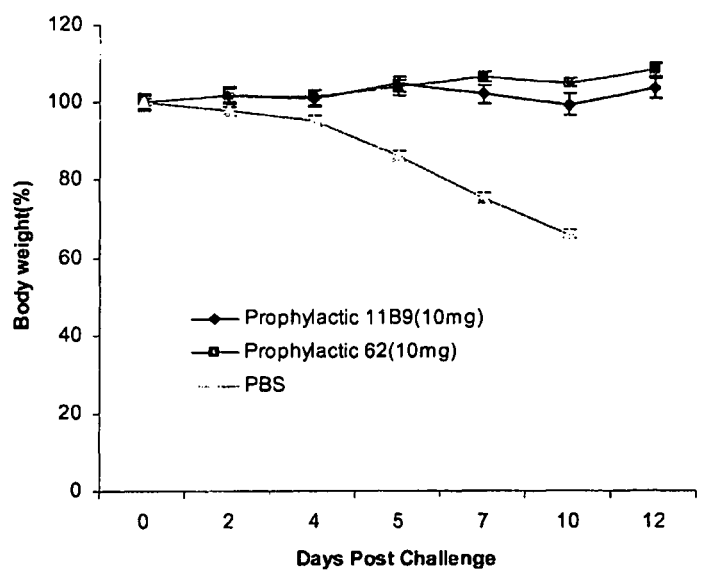

Prophylactic Treatment with mAb 11B9 and mAb 62 Protect Mice from Lethal Viral Challenge The protective efficacy of mAb 11B9 and mAb 62 were examined individually in mice challenged with adapted H7N7 virus (A/Netherlands/219/03). All mice pre-treated with a single dose of 10 mg/kg of either mAb were protected from death following the lethal challenge with 5MLD50 of H7N7 virus (A/Netherlands/219/03) (100% protection), whereas all untreated control mice were died from viral infection by day 7 after challenge (FIG. 1A). All mice pre-treated with a single dose of 10 mg/kg of either mAb showed less than 1% body weight loss after virus challenge. Most of these mAb-treated mice gained body weight up to 8% after virus challenge, while the group of mice without mAb treatment showed significant body weight loss after virus challenge (>30%) (FIG. 1B).

Example 5

Production of Antibodies and Antibody Fragments

The monoclonal antibodies of the present invention can be produced by any technique that provides for the production of antibody molecules by continuous cell lines in culture. Such methods include, but are not limited to, the hybridoma technique originally developed in 1975 by Kohler and Milstein (Nature 256:495-497), as well as the trioma technique, the human B-cell hybridoma technique (Kozbor et al., 1983, Immunology Today 4:72) and the EBV-hybridoma technique to produce human monoclonal antibodies (Cole et al., in Monoclonal Antibodies and Cancer Therapy Alan R. Liss, Inc., pp 77-96 (1985)). Human antibodies can be used and can be obtained by using human hybridomas (Cote et al., 1983, Proc. Nat=l. Acad. Sci. U.S.A., 80:2026-2030) or by transforming human B cells with EBV virus in vitro (Cole et al., 1985, in Monoclonal Antibodies and Cancer Therapy, Alan R. Liss, pp. 77-96). Moreover, techniques developed for the production of "chimeric antibodies" or "humanized antibodies" (Morrison et al., 1984, J Bacteriol. 159-870; Neuberger et al., 1984, Nature 312:604-608; Takeda et al., 1985, Nature 314:452-454) by introducing sequences from a murine antibody molecule of the present invention, e.g., mAb 11B9 or mAb 62, together with genes from a human antibody molecule of appropriate biological activity can be used. Chimeric antibodies are those that contain a human Fc portion and a murine (or other non-human) Fv portion. Humanized antibodies are those in which the murine (or other non-human)

complementarity determining regions (CDR) are incorporated into a human antibody. Both chimeric and humanized antibodies are monoclonal. Such human or humanized chimeric antibodies are preferred for use in in vivo diagnosis or therapy of human diseases or disorders.

According to the invention, techniques described for the production of single chain antibodies (U.S. Pat. No. 4,946, 778) can be adapted to provide single chain antibodies of the present invention. An additional embodiment of the invention utilizes the techniques described for the construction of Fab expression libraries (Huse et al., 1989, *Science* 246: 1275-1281) to allow rapid and easy identification of monoclonal Fab fragments with the desired specificity for an antibody of the present invention, or its derivatives, or analogs.

Antibody fragments that contain the idiotype of the antibody molecule can be generated by known techniques. For example, such fragments include but are not limited to: the F(ab=)$_2$ fragment which can be produced by pepsin digestion of the antibody molecule; the Fab=fragments which can be generated by reducing the disulfide bridges of the F(ab=)$_2$ fragment, and the Fab fragments which can be generated by treating the antibody molecule with papain and a reducing agent. Such antibody fragments can be generated from any of the polyclonal or monoclonal antibodies of the invention.

In the production of antibodies, screening for the desired antibody can be accomplished by techniques known in the art, e.g., radioimmunoassay, ELISA (enzyme-linked immunosorbent assay), immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), immunofluorescence assays and immunoelectrophoresis assays, etc. In one embodiment, antibody binding is detected by detecting a label on the primary antibody. In another embodiment, the primary antibody is detected by detecting binding of a secondary antibody or other reagent to the primary antibody. In a further embodiment, the secondary antibody is labeled. Means are known in the art for detecting binding in an immunoassay.

Example 6 mAb 62 is an Efficient Neutralizing Antibody Against Different H7 Strains

A panel of Mabs against influenza hemagglutinin was screened for efficient recognition of different strains of H7 viruses. Based on the results of the HI assay, mAb 62 was selected for further studies due to its high HI activity (Table 1) against a wide range of H7 viruses from birds and humans. The mAb belongs to the IgG1 isotype. The virus neutralizing activity of mAb 62 was further confirmed to be positive against six representative H7 strains, including one human H7N9 strain (Table 4). Based on this, the amino acids involved in forming the epitope of mAb 62 were analyzed using selection of neutralization escape mutants. A/chicken/Malaysia/94 H7N1 virus was used as parental virus for the selection. Sequences of the complete HA genes isolated from multiple escape variants were compared with the parental virus. It was found that mutants with mAb 62 carried mutations at either amino acid 175 (Lys to Glu) or amino acid 227 (Glu to Gly). The numbering of amino acid on HA starts from "ATG" and includes the signal peptide.

TABLE 4

Hemagglutination Inhibition (HI) and Virus Neutralization (VN) Titer of mAb 62 (100 ug/ml) Against Different H7 Viruses

| Virus | Subtype | HI titer | VN titer |
| --- | --- | --- | --- |
| A/Chicken/Malaysia/94 | H7N1 | 256 | 640 |
| A/Canada/rv504/04 | H7N3 | 64 | 160 |
| A/quail/Aichi/4/09 | H7N6 | 128 | 160 |
| A/duck/Hokkaido/1/10 | H7N7 | 256 | 640 |
| A/Netherlands/219/03 | H7N7 | 256 | 1280 |
| A/Shanghai/1/13 | H7N9 | 256 | 640 |
| A/Puerto Rico/8/34 | H1N1 | <8 | <20 |

HI titer below 8 and VN titer below 20 indicate negative activity.

In order to determine the significance of the neutralization epitope of mAb 62, the protein polymorphism of H7 was studied, taking into account all H7 sequences in the NCBI database. On the 175th amino acid, lysine and asparagine appear in more than 99.9% of H7 AIV strains listed. Lysine is the most dominant amino acid with the frequency of 97.9% among avian H7 strains and 100% among human 117s, including strains from the recent H7N9 outbreak in eastern China. This finding suggests the potential of the mAb 62 to be used to recognize or neutralize all the H7 human strain identified so far and to be further formulated as an effective H7 AIV treatment.

Example 7

Effective Prophylactic Immunization by a Single Dose of mAb 62 Against a Lethal Challenge of H7

The prophylactic efficacy of mAb 62 was evaluated against a challenge with 5 MLD$_{50}$ of H7N7 virus (A/Netherlands/219/03). Groups of mice (n=5) were inoculated via either the intraperitoneal or intranasal route with different concentrations (2.5 mg/kg, 5 mg/kg and 10 mg/kg) of mAb 62, one day prior to viral challenge. The negative control group of mice (treated with PBS only) showed the most rapid decline in body weight (above 25%) and died from complications associated with infection by day 8 post challenge. All of the mice pre-treated via either route with a single dose of mAb 62 showed less than 6% (FIGS. 2A and 2C) loss of body weight and a 100% survival rate (FIGS. 2B and 2D) against the lethal challenge of H7 virus. In mucosal route, immunization with 2.5 mg/kg of mAb 62 was sufficient for 100% protection against the H7 challenge with a loss in body weight of lower than 5%. The intraperitoneal dose of 5 mg/kg of mAb 62 was able to prevent significant body weight loss in challenged mice while a 6% reduction in body weight was observed in mice with the lower IP dose of 2.5 mg/kg.

Example 8

Effective Therapeutic Immunization by Intranasal Administration of mAb 62

Figure 3:
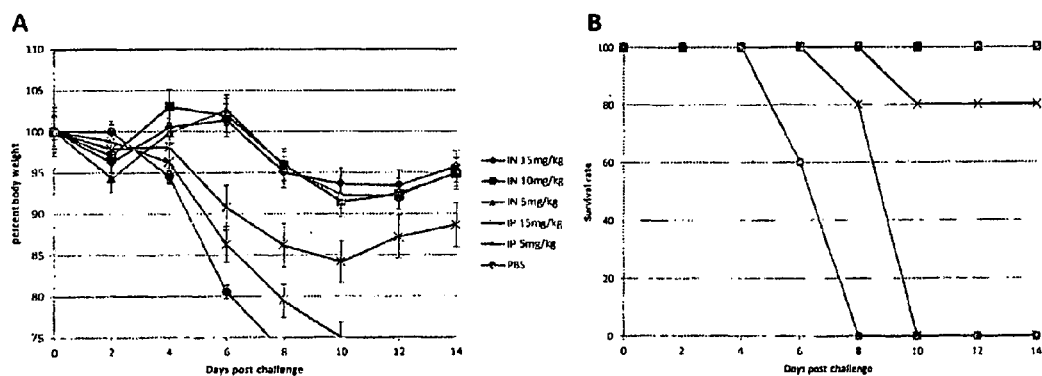

The therapeutic efficacy of mAb 62 was evaluated against a challenge with 5 MLD50 of H7N7 virus (A/Netherlands/219/03). Groups of mice (n=5) were inoculated via either the intraperitoneal or intranasal route with different concentrations (5 mg/kg, 10 mg/kg and 15 mg/kg) of mAb 62, one day post viral challenge. The negative control group of mice (treated with PBS only) showed the most rapid decline in body weight (above 25%) and died from complications associated with infection by day 8 post challenge. All of the mice intransally treated with a single dose of mAb 62 showed less than 10% (FIG. 3A) loss of body weight and a 100% survival rate (FIG. 3B) against the lethal challenge of H7 virus. Intranasal doses from 5 mg/kg to 15 mg/kg did not present significant differences in efficacy of the treatment. The intraperitoneal dose of 5 mg/kg of mAb 62 failed to protect mice from death 10 days post challenges. In the group with a higher intraperitoneal dose of 15 mg/kg, 4 mice survived with more than 15% loss of body weight.

Example 9

Therapeutic Efficacy of a Single Dose Versus Two Doses of mAb 62 Against a Higher Challenge Dose of H7

Figure 4:
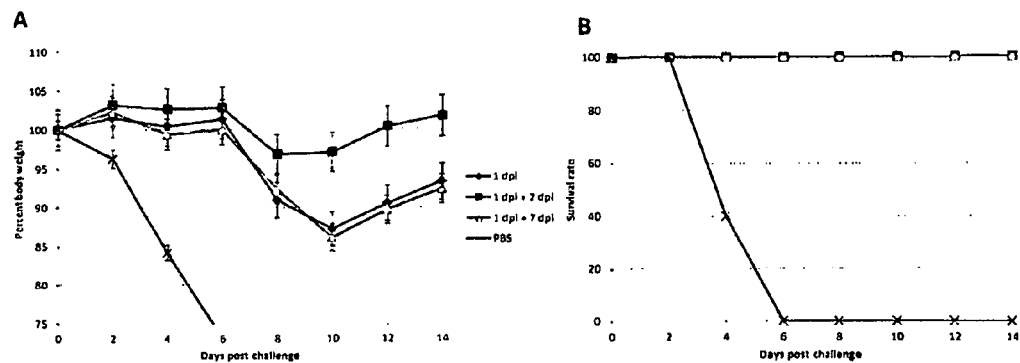

In order to test the therapeutic potential of mAb 62 against the higher challenge dose of 10 $MLD_{50}$ of H7N7, the efficacy of the single nasal dose one day post challenge was compared with that in mice treated with double nasal doses of 10 mg/kg mAb 62 each time at different time points (1 dpi and 2 dpi; 1 dpi and 7 dpi). Upon the challenge with 10 $MLD_{50}$ of H7N7 virus (A/Netherlands/219/03), the negative control group of mice (treated with PBS only) showed a more rapid decline in body weight (above 25%) than the infections with 5 $MLD_{50}$ and died from complications associated with infection by day 6 post challenge. As shown in FIGS. 4A and 4B, all the mice treated intranasally with the single dose of 10 mg/kg of mAb 62 survived the infection of 10 $MLD_{50}$ with around 13% loss in body weight. A double-nasal dose one day and two days post infection successfully protected all the infected mice with a loss in body weight of less than 5%. Moreover, the group of mice that received the double dose of mAb 62 (1 dpi and 2 dpi) regained their body weight more rapidly (within 8 days) when compared to the mice that received a single dose, which regained their body weight only by 10 days after the viral infection. No enhancement in therapeutic efficacy was observed in mice with a double nasal dose one day and seven days post infection. The mice in this group presented with a similar loss and recovery in body weight as the group receiving a single dose.

Example 10

Figure 5:
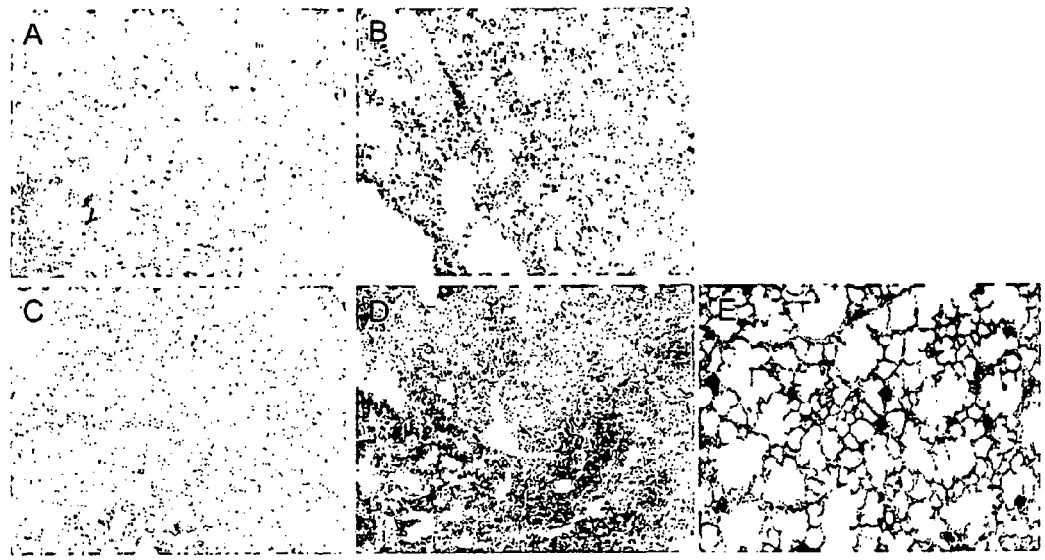

Therapeutics with mAb 62 Via the Intranasal Route was More Effective than Intraperitoneal Treatment As differences between intranasal and intraperitoneal therapeutics were observed based on mouse mortality and body weight, further studies were perform to confirm the better protection efficacy of intranasal administration. Histopathology studies were conducted on the lungs of mice treated intranasally or intraperitoneally with mAb 62. As shown in FIGS. 5C and 5D, pulmonary lesions developed with the progressive infection in the late stage in H7N7 infected mice without treatment, consisting of moderate to severe necrotizing bronchitis and histiocytic alveolitis with associated pulmonary edema. Meanwhile, the uninfected mice lacked lesions in the lungs (FIG. 5E). Lungs collected on day 14 post infection, from mice treated intranasally with 15 mg/kg mAb 62 showed no lung pathology and looked similar to the uninfected control (FIG. 5A), while moderate bronchitis was present in the lungs of mice intraperitoneally treated with 15 mg/kg of mAb 62 (FIG. 5B).

Figures 6, 8:
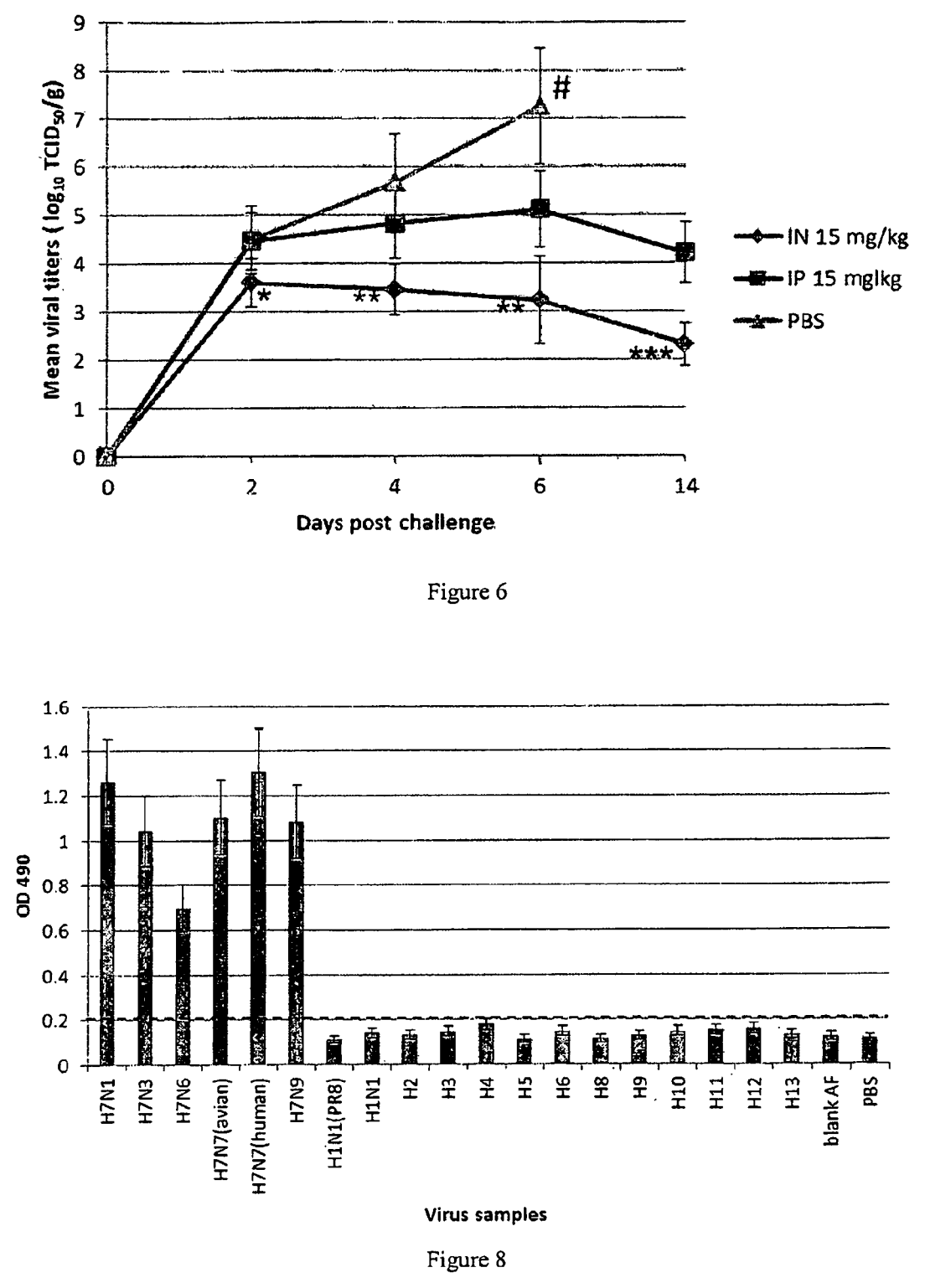

Moreover, virus load in lungs was evaluated in H7 infected or treated mice. The kinetics of viral replication was determined by measuring the viral titers in the mouse lungs on days 2, 4, 6 and 14 post infection (FIG. 6). The virus titers were most elevated on day 6 after viral challenge when the highest virus titers of more than $10^{7.15}$ were detected in the infected but untreated mice which died within the following two days. The mice treated intranasally with a single dose of 15 mg/kg of mAb 62 showed decreasing viral loads from day 2 post infection. However those mice treated intraperitoneally with the same antibody dose showed the decrease in virus load only by day 6 post-infection. Virus titers in intraperitoneally treated mice were higher than those in the intranasal group at every time point, indicating that intranasal treatment reduced the virus load from the start of the infection. All these findings confirm that intranasal therapeutics with mAb 62 is more effective than intraperitoneal treatment against H7N7 HPAI virus.

Example 11 mAbs 62 and 11B9 Recognize Conserved Neutralizing Epitopes on H7 AIVs

A panel of mAbs against influenza hemagglutinin was screened for efficient recognition of different strains of H7 viruses. Based on the results of the HI assay and virus neutralization (Table 5), mAb 62 and mAb 11B9 were selected for further studies due to their high HI activity against a wide range of H7 viruses from birds and humans, including strains from the recent H7N9 outbreak in eastern China. Both the mAbs belong to the IgG1 isotype. The virus neutralizing activity of mAb 62 and mAb 11B9 was further confirmed to be positive against H7 AIVs. Based on this, the amino acids involved in forming the epitope of mAb 62 and mAb 11B9 were analyzed using selection of neutralization escape mutants. A/chicken/Malaysia/94 H7N1 virus was used as parental virus for the selection. Sequences of the complete HA genes isolated from multiple escape variants were compared with the parental virus. It was found that mutants generated with mAb 62 carried mutations at either amino acid 175 (Lys to Glu) or amino acid 227 (Glu to Gly). mAb 11B9 carried mutations at either amino acid 136 (Ser to Gly), or amino acid 137 (Gly to Arg) or amino acid 227 (Glu to Gly). The numbering of amino acid on HA starts from "ATG" and includes the signal peptide.

TABLE 5

Hemagglutination Inhibition (HI) and Virus Neutralization (VN) Titer of mAb 62 and mAb 11B9 (200 μg/ml) Against Different H7 Viruses Without Any Cross Reactivity Against Any Other Subtypes

| Virus | Subtype | HI titer (mAb 62, 11B9) | VN titer (mAb 62, 11B9) |
|---|---|---|---|
| A/Chicken/Malaysia/94* | H7N1 | 256, 256 | 640, 640 |
| A/Canada/rv504/04 | H7N3 | 128, 256 | 320, 640 |
| A/quail/Aichi/4/09 | H7N6 | 64, 64 | 80, 80 |
| A/duck/Hokkaido/1/10 | H7N7 | 128, 256 | 320, 640 |
| A/Netherlands/219/03 | H7N7 | 256, 256 | 640, 1280 |
| A/Shanghai/1/13* | H7N9 | 64, 128 | 160, 320 |
| A/Puerto Rico/8/34 | H1N1 | <8, <8 | <20, <20 |
| A/TLL51/Singapore/09 | H1N1 | <8, <8 | <20, <20 |
| A/duck/Nanchang/4-184/2000 | H2N9 | <8, <8 | <20, <20 |
| A/Chicken/Malaysia/02* | H3N2 | <8, <8 | <20, <20 |
| A/Chicken/Malaysia/92* | H4N1 | <8, <8 | <20, <20 |
| A/Vietnam/VN1203/03 | H5N1 | <8, <8 | <20, <20 |
| A/Shorebird/DE/12/04 | H6N8 | <8, <8 | <20, <20 |
| A/duck/Yangzhou/02/05 | H8N4 | <8, <8 | <20, <20 |
| A/chicken/Malaysia/98* | H9N2 | <8, <8 | <20, <20 |
| A/mandarin duck/Malaysia/98* | H10N5 | <8, <8 | <20, <20 |

TABLE 5-continued

Hemagglutination Inhibition (HI) and Virus Neutralization (VN) Titer of mAb 62 and mAb 11B9 (200 μg/ml) Against Different H7 Viruses Without Any Cross Reactivity Against Any Other Subtypes

| Virus | Subtype | HI titer (mAb 62, 11B9) | VN titer (mAb 62, 11B9) |
|---|---|---|---|
| A/pintail/Alberta/84/2000 | H11N9 | <8, <8 | <20, <20 |
| A/pintail/Alberta/49/03 | H12N5 | <8, <8 | <20, <20 |
| A/gull/Maryland/704/1977 | H13N6 | <8, <8 | <20, <20 |

HI titer below 8 and VN titer below 20 indicated negative activity.
*wild type virus.

In order to determine the significance of the neutralization epitopes of mAb 62 and 11A9, the protein polymorphism of H7 was studied (Table 6), taking into account all H7 sequences in the NCBI database. On the 175th amino acid, lysine and asparagine appear in more than 99.9% of H7 AIV strains listed. Lysine is the most dominant amino acid with the frequency of 97.9% among avian H7 strains and 100% among human H7s. On the 136th amino acid, serine exists in 96.6% of avian strains and 100% of human H7 strains, while glycine on the 137th amino acid exists in 99.9% of avian H7 and 100% of human strains. This finding indicates that the two mAbs are able to recognize or neutralize all the H7 human strain identified so far, suggesting their potential for universal H7 AIV detection.

TABLE 6

Epitope Frequency in Both Human and Avian H7 Strains

| mAb | Amino acid | Human frequency | Avian frequency |
|---|---|---|---|
| 11B9 | 136 Ser | 100% | 96.6% |
|  | 137 Gly | 100% | 99.9% |
| 62 | 175 Lys | 100% | 97.9% |

Example 12

Development of the Dual Function ELISA

Figure 7:
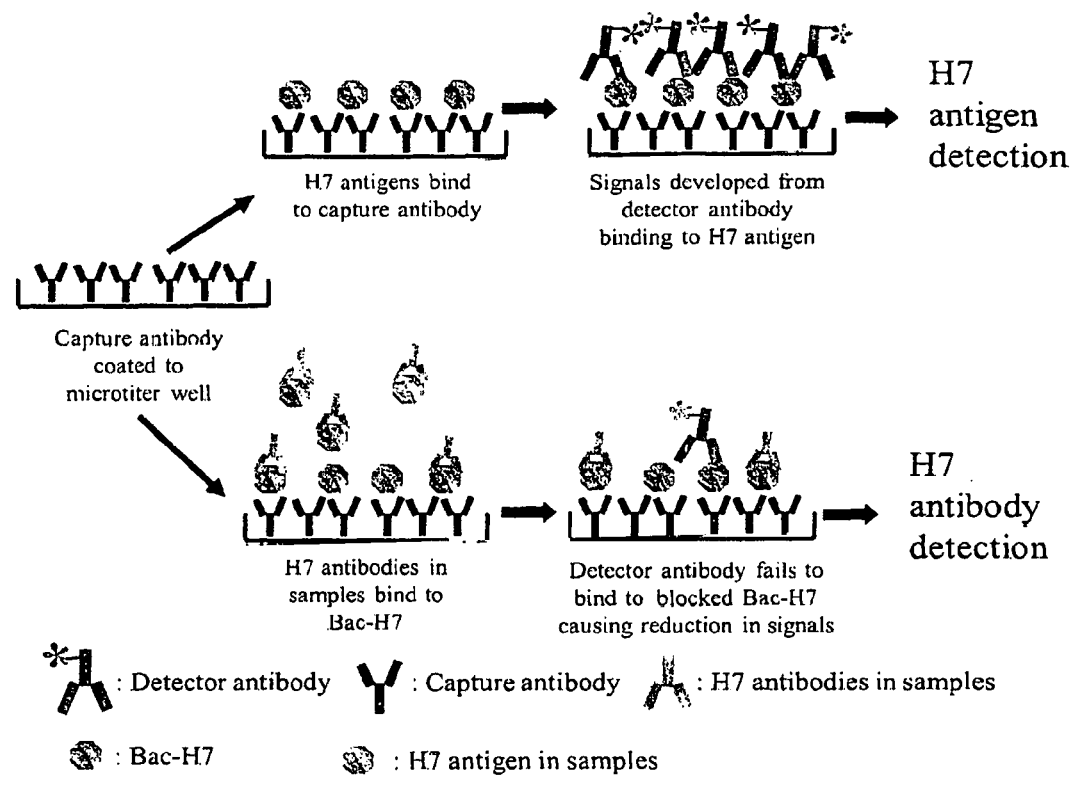

The dual-function-ELISA was operated as shown in FIG. 7. H7 antigen can be detected in an AC-ELISA based on H7 specific mAbs. mAb 62 was randomly selected as the detector antibody and mAb 11B9 was used as the capture antibody due to their equivalent performance in the reversible use in H7 AC-ELISA. Optimal concentrations of mAbs 62 and 11B9 for detection and capture were determined by two-way titration of mAb concentrations. The combination that gave the highest signal-to-noise ratio was determined to be 0.5 μg/well of capture mAb 11B9 and 0.9 μg/well of mAb 62 for detection. The tested virus was considered to be positive with H7 antigen in the dual ELISA when the absorbance was three times higher than that of the non-H7 viruses.

Serum antibodies to H7 can be detected by virtue of their ability to block the recognition of the target epitope by a H7 specific mAb an ELISA assay. To combine this assay to the AC-ELISA, serum samples were incubated with the fixed amount of recombinant baculovirus, which displays H7 on the virus surface, before being loaded to the plate coated with the capture mAb. H7 antibody titers in samples were determined based on the reduction of the detected H7 baculovirus. Different concentrations of H7 baculovirus were tested before confirming the optimal concentration at 8 HAU. Serum panels from normal or H7 immunized chicken and mice were used to determine the cut-off value. First, a panel of normal serum samples from 16 chicken and 20 mice lacking antibodies to H7 was used to determine the baseline of non-specific reduction in mAb 62 binding to H7 antigen in the dual ELISA. Mean reduction of dual ELISA readings was 6.5% for this serum panel, with a standard deviation (SD) of 7.1. Specific blocking activities can be determined with 95% confidence if a "cut-off value" of ≥30% is set for serum samples. The latter was obtained by adding 3 SD to the mean 6.5% blocking (6.5+21.3=27.8%). In the test, the dilution factor of each serum sample at was recorded when it presented ≥30% signal blocking rate. Additionally, the blocking rate of each sample diluted at 20 times was recorded for comparison.

Example 13

Specificity and Sensitivity of H7 Antigen Detection by the Dual Function ELISA

The specificity of H7 antigen detection by the dual ELISA was tested with 6 H7 strains from humans and avian species and 13 representative non-H7 subtype influenza virus strains from different regions and years, including pandemic influenza and avian influenza virus strains circulating in humans (FIG. 8). Viruses of H7 or HA subtypes not available in our laboratory were rescued by reverse genetics with the six internal genes from A/Puerto Rico/8/34. The reactivity and specificity of H7 antigen detection in the dual-ELISA were examined with 100 μl of PBS containing the H7 strains adjusted to an HA titer of 8. Non-H7 viruses with HA titers of ≥16 were used in order to eliminate false-positive results. No cross-reactivity was observed for any of the non-H7 subtype viruses tested.

Figures 9, 10:
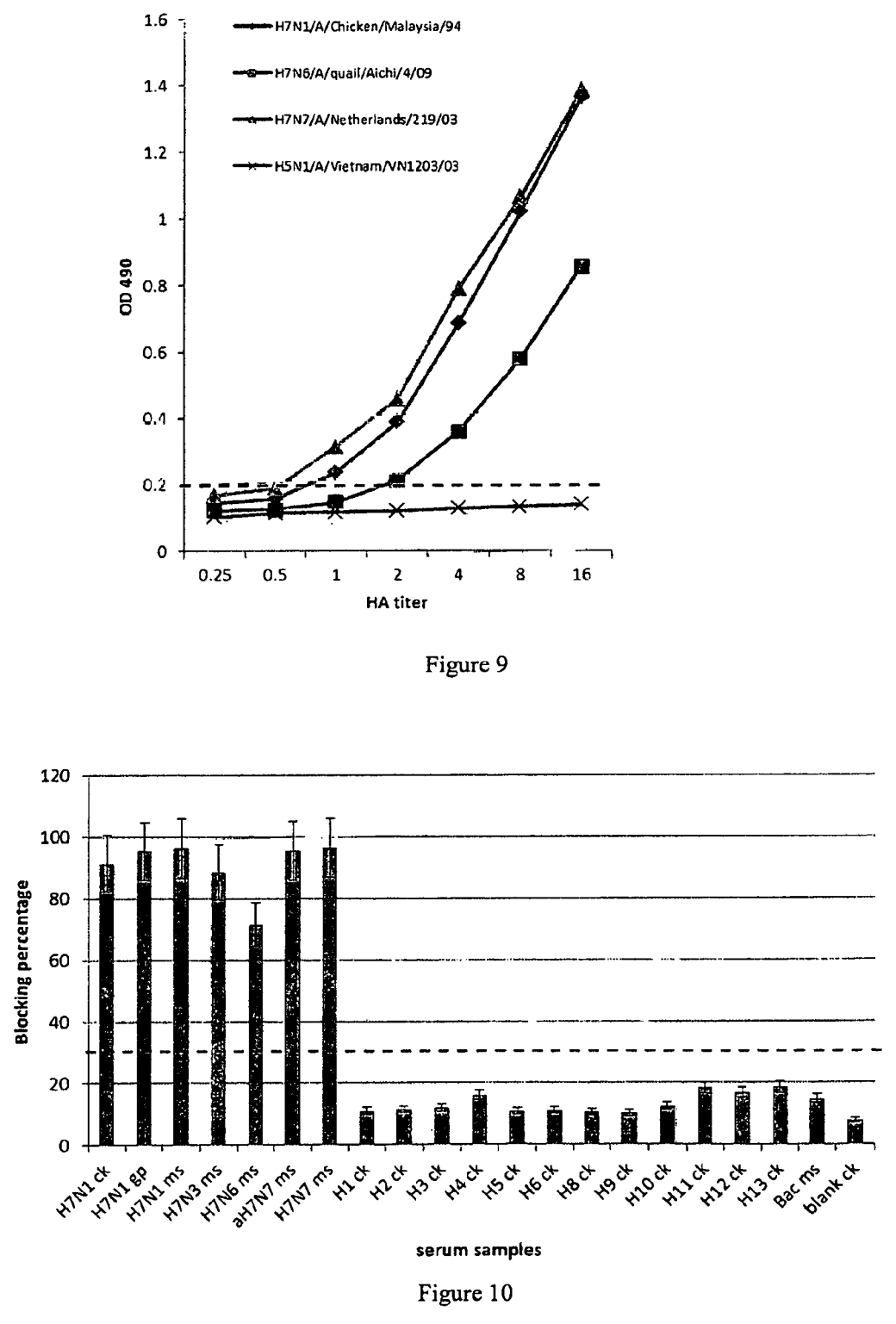

The analytical sensitivity of H7 antigen detection in the dual ELISA was determined against four different H7 strains which had absorbance readings ranging from 0.7 to 1.3 at 8 HAU (FIG. 9). The three selected H7 viruses were diluted serially for the determination of the detection limit based on virus HA titer. With a cut-off value of 0.2, the detection limit was determined to be 100 μl of sample containing 1 HA titer of virus for viruses that had average and higher-than-average absorbance, while it was 2 HA titers for viruses that had lower-than-average absorbance. The detection limit of HI test for influenza virus was determined at 2 HAU (100 ul) and subtype cross-reactivity were observed.

Example 14

Specificity of H7 Antibody Detection by the Dual Function ELISA

The specificity of the H7 detection by the dual ELISA was investigated using a panel of antisera from experimentally immunized chickens, mice and guinea pigs. Animal sera collected 10 days after the $2^{nd}$ immunization were first diluted to obtain HI titer of 16 to the homologous virus to normalize antibody concentrations prior to use in EB-ELISA. Sera from chicken immunized with H7N1 influenza viruses (FIG. 10) presented ≥85% inhibition in mAb 62 binding, while sera from chickens immunized with H1-H6 and H8-H13 showed maximum blocking of 10%, well below the 30% threshold established for samples containing H7 specific antibodies. No inhibition was detected with sera immunized with wild type baculovirus. Positive inhibition was also observed with all mouse sera from individual immunizations with 4 different H7 strains, indicating the assay is specific to detect H7 antibodies. All animal sera from H7 immunization, including chicken, mouse and guinea pigs, showed positive blocking in the dual ELISA, indicating the assay is effective for sera from any species. These results indicate that the antibody detection in the dual ELISA could positively identify serum samples containing antibodies to H7 without any cross reaction to sera from other subtypes.

Example 15

Sensitivity of H7 Antibody Detection by the Dual Function ELISA

The sensitivity of H7 antibody detection in the dual ELISA was primarily determined by comparison to virus neutralization and HI using purified mAb 62. As shown in Table 7, in the dual ELISA, 40 ng of mAb 62 was sufficient to reach the endpoint corresponding to a blocking rate of more than 30%, while at least 160 ng of the same mAb 62 was needed to neutralize 100 TCID50 of H7N7 (A/Netherlands/219/03) virus or inhibit hemagglutination. Additional comparisons of the dual ELISA and virus neutralization in antibody detection were made using H7 immunized mice sera (Table 8). The neutralization titers of mice sera after only one immunization with variant H7 MV strains individually ranged from 40 to 320 against H7N7 (A/Netherlands/219/03). The same batch of sera was tested in the dual ELISA where the endpoint titers ranged from 100 to 1000. No positive activity was detected for pre-immunization serum samples by either test. The comparison indicated that the dual ELISA was able to detect a lower concentration of H7 specific antibody and present a higher signal titer than virus neutralization.

TABLE 7

The Detection Limits of the Dual Function ELISA in Antibody Detection, HI and Microneutralization Assay Based on a Neutralizing mAb

| EB-ELISA | | Microneutralization | | HI | |
|---|---|---|---|---|---|
| mAb amount | Inhibition rate | mAb amount | Titer | mAb amount | Titer |
| 5 µg | 92.6% | 5 µg | 640 | 5 µg | 256 |
| 1 µg | 64.87% | 1.25 µg | 160 | 1.25 µg | 64 |
| 0.2 µg | 48.99% | 0.313 µg | 40 | 0.313 µg | 16 |
| *0.04 µg* | *31.05%* | *0.16 µg* | *20* | *0.16 µg* | *8* |
| 0.008 µg | 12.84% | 0.08 µg | <20 | 0.08 µg | <8 |

The detection limit of each test is indicated in bold and italics format.

TABLE 8

Comparison Between the Dual Function ELISA and Virus Neutralization in Antibody Detection With Pooled Mice Sera After a Single H7 Immunization

| Virus immunized | Inhibition in dual ELISA at 1:20 dilution | Dual ELISA titer at 30% cut-off | Virus neutralization titer |
|---|---|---|---|
| H7N3/A/Canada/rv504/04 | 91.47% | 500 | 160 |
| H7N6/A/quail/Aichi/4/09 | 61.64% | 100 | 40 |
| H7N7/A/duck/Hokkaido/1/10 | 92.84% | 500 | 160 |

TABLE 8-continued

Comparison Between the Dual Function ELISA and Virus Neutralization in Antibody Detection With Pooled Mice Sera After a Single H7 Immunization

| Virus immunized | Inhibition in dual ELISA at 1:20 dilution | Dual ELISA titer at 30% cut-off | Virus neutralization titer |
|---|---|---|---|
| H7N7/A/Netherlands/219/03 | 94.68% | 1000 | 320 |
| Pre-immunization sera | 4.14% | <20 | <20 |

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

Abbas M A, Spackman E, Fouchier R, Smith D, Ahmed Z, et al. (2011) H7 avian influenza virus vaccines protect chickens against challenge with antigenically diverse isolates. Vaccine 29: 7424-7429.

Brown, E. G. (1990). Increased virulence of a mouse-adapted variant of influenza A/FM/1/47 virus is controlled by mutations in genome segments 4, 5, 7, and 8. *J Virol* 64(9), 4523-33.

Chothia C and Lesk A M (1987). "Canonical structures for the hypervariable regions of immunoglobulins.", J Mol Biol 196:901-917.

Gambaryan A S, Matrosovich T Y, Philipp J, Munster V J, Fouchier R A, et al. (2012) Receptor-binding profiles of H7 subtype influenza viruses in different host species. J Virol 86: 4370-4379.

He, F., and Kwang, J. (2013). Monoclonal Antibody Targeting Neutralizing Epitope on H5N1 Influenza Virus of Clade 1 and 0 for Specific H5 Quantification. Influenza Res Treat 2013, 360675.

He, F., Du, Q., Ho, Y., and Kwang, J. (2009). Immunohistochemical detection of Influenza virus infection in formalin-fixed tissues with anti-H5 monoclonal antibody recognizing FFWTILKP. J Virol Methods 155(1), 25-33.

He, F., Soejoedono, R. D., Murtini, S., Goutama, M., and Kwang, J. (2010). Complementary monoclonal antibody-based dot ELISA for universal detection of H5 avian influenza virus. BMC Microbiol 10, 330.

Hieter P A, Max E E, Seidman J G, Maizel J V Jr, Leder P (1980). "Cloned human and mouse kappa immunoglobulin constant and J region genes conserve homology in functional segments." Cell 22:197-207.

Ho, H. T., Qian, H. L., He, F., Meng, T., Szyporta, M., Prabhu, N., Prabakaran, M., Chan, K. P., and Kwang, J. (2009). Rapid detection of H5N1 subtype influenza viruses by antigen capture enzyme-linked immunosorbent assay using H5- and N1-specific monoclonal antibodies. Clin Vaccine Immunol 16(5), 726-32.

Huston J S, Levinson D, Mudgett-Hunter M, Tai M S, Novotný J, Margolies M N, Ridge R J, Bruccoleri R E, Haber E, Crea R, et al. (1988). "Protein engineering of antibody binding sites: recovery of specific activity in an anti-digoxin single-chain Fv analogue produced in Escherichia coli." Proc. Nat. Acad. Sci. USA, 85:5879-5883.

Jadhao S J, Achenbach J, Swayne D E, Donis R, Cox N, et al. (2008) Development of Eurasian H7N7/PR8 high growth reassortant virus for clinical evaluation as an inactivated pandemic influenza vaccine. Vaccine 26: 1742-1750.

Johnson G and Wu T T (2001). "Kabat Database and its applications: future directions." Nucleic Acids Res 29:205-206.

Kabat E A et al. (1991). Sequences of Immunological Interest, Fifth Edition, National Institute of Health, Bethesda, Md.

Kaverin N V, Rudneva I A, Govorkova E A, Timofeeva T A, Shilov A A, et al. (2007). Epitope mapping of the hemagglutinin molecule of a highly pathogenic H5N1 influenza virus by using monoclonal antibodies. *J Virol* 81:12911-12917.

Khaw, B. A., Strauss, H. W., Carvalho, A., Locke, E., Gold, H. K., Haber, E. (1982). "Technetium-99m labeling of antibodies to cardiac myosin Fab and to human fibrinogen." J Nucl Med 23:1011-1019.

Min J Y, Vogel L, Matsuoka Y, Lu B, Swayne D, et al. (2010) A live attenuated H7N7 candidate vaccine virus induces neutralizing antibody that confers protection from challenge in mice, ferrets, and monkeys. J Virol 84: 11950-11960.

Prabakaran M, Prabhu N, He F, Hongliang Q, Ho H T, et al. (2009) Combination therapy using chimeric monoclonal antibodies protects mice from lethal H5N1 infection and prevents formation of escape mutants. PLoS One 4: e5672.

Prabakaran M, He F, Meng T, Madhan S, Yunrui T, et al. (2010).: Neutralizing epitopes of influenza virus hemagglutinin: target for the development of a universal vaccine against H5N1 lineages. *J Virol* 84:11822-11830.

Prabhu, N., Prabakaran, M., Hongliang, Q., He, F., Ho, H. T., Qiang, J., Goutama, M., Lim, A. P., Hanson, B. J., and Kwang, J. (2009). Prophylactic and therapeutic efficacy of a chimeric monoclonal antibody specific for H5 haemagglutinin against lethal H5N1 influenza. *Antivir Ther* 14(7), 911-21.

Rader C, Cheresh D A, Barbas C F 3rd (1998). "A phage display approach for rapid antibody humanization: designed combinatorial V gene libraries." Proc Natl Acad Sci USA 95:8910-8915.

Reed, L. J. and Muench, H. (1938). "A simple method of estimating fifty percent endpoints". *The American Journal of Hygiene* 27: 493-497.

Riechmann L, Clark M, Waldmann H, Winter G (1988). "Reshaping human antibodies for therapy." Nature 332:323-327.

Rousseaux J, Rousseaux-Prevost R, Bazin H (1986). "Optimal conditions for the preparation of proteolytic fragments from monoclonal IgG of different rat IgG subclasses." Methods Enzymology 121:663-69, Academic Press.

What is claimed is:

1. A monoclonal antibody or antibody fragment which specifically binds to a neutralizing conformational epitope of H7 hemagglutinin, wherein (a) the neutralizing conformational epitope comprises amino acid 136Ser, 137Gly and amino acid 227Glu of the amino acid sequence set forth in SEQ ID NO:2 and wherein the monoclonal antibody is monoclonal antibody 11B9 as produced by hybridoma 11B9 which is deposited with CellBank Australia with Accession Number CBA20120022 or (b) the neutralizing conformational epitope comprises amino acid 175Lys and amino acid 227Glu of the amino acid sequence set forth in SEQ ID NO:2 and wherein the monoclonal antibody is monoclonal antibody 62 as produced by hybridoma 62 which is deposited with CellBank Australia with Accession Number CBA20120023.

2. The monoclonal antibody of claim 1, wherein the monoclonal antibody is monoclonal antibody 11B9.

3. The monoclonal antibody of claim 1, wherein the monoclonal antibody is monoclonal antibody 62.

4. A method for detecting an influenza A H7 subtype virus in a biological specimen which comprises contacting the specimen with a first antibody, wherein the first antibody is a monoclonal antibody or antibody fragment of claim 1, and determining the presence or absence of an influenza A H7 subtype virus.

5. The method of claim 4 which further comprises contacting the specimen with a second antibody that specifically binds to an epitope of H7 hemagglutinin of the influenza A H7 subtype virus, wherein said second antibody contains or is conjugated to a detectable element, wherein the contacting with the second antibody is performed before the determination.

6. The method of claim 5, wherein the first antibody is immobilized onto a solid surface.

7. The method of claim 5, wherein the first antibody is one of monoclonal antibody 11B9 or monoclonal antibody 62 and the second antibody is the other of said monoclonal antibody 11B9 or monoclonal antibody 62.

8. The method of claim 5, wherein the second antibody contains a radioactive atom, is conjugated to a fluorescent molecule, or is conjugated to an enzyme.

9. The method of claim 4, wherein the influenza A virus is an H7N7 subtype.

10. A kit for detecting an influenza A H7 subtype virus in a biological specimen which comprises a first antibody, wherein the first antibody is the monoclonal antibody or antibody fragment of claim 1 together with instructions for performing an assay to detect the influenza A virus.

11. The kit of claim 10, which further comprises a second antibody that specifically binds to an epitope of H7 hemagglutinin of the influenza A H7 subtype virus, wherein said second antibody contains or is conjugated to a detectable element.

12. The kit of claim 11, wherein the first antibody is immobilized onto a solid surface.

13. The kit of claim 11, wherein the first antibody is one of monoclonal antibody 11B9 or monoclonal antibody 62 and the second antibody is the other of said monoclonal antibody 11B9 or monoclonal antibody 62.

14. The kit of claim 11, wherein the second antibody contains a radioactive atom, is conjugated to a fluorescent molecule, or is conjugated to an enzyme.

15. The kit of claim 10, wherein the influenza A virus is an H7N7 subtype.

16. A composition comprising an agent and a pharmaceutically acceptable diluent or carrier, wherein the agent is the monoclonal antibody or antibody fragment of claim 1.

17. A method of reducing influenza H7 subtype virus infection in a subject, or lowering the risk of influenza H7 subtype virus infection in a subject, or inhibiting infection of a subject by one or more influenza H7 subtype virus strains or isolates, or prophylaxis of influenza infection or disease by one or more influenza H7 subtype virus strains or isolates which comprises administering to a subject in need thereof, a therapeutically effective amount of an agent, wherein the agent is the monoclonal antibody or antibody fragment of claim 1.

18. The method of claim 17, wherein the subject is immunocompromised, an infant, a young child or elderly.

19. The method of claim 18, wherein the administration provides a therapeutic benefit.

20. The method of claim 19, wherein the therapeutic benefit comprises (a) inhibiting increases in influenza virus titer, (b) decreasing influenza virus titer, (c) inhibiting increases in influenza virus replication, (d) decreasing influenza virus replication, (e) inhibiting increases in influenza virus proliferation or decreasing influenza virus proliferation, (f) decreasing progression, severity, frequency, duration or probability one or more symptoms or complications associated with influenza virus infection in a subject or (g) hastening a subject's recovery from influenza virus infection.

21. The method of claim 20, wherein a symptom or complication is selected from chills, fever, cough, sore throat, nasal congestion, sinus congestion, nasal infection, sinus infection, body ache, head ache, fatigue, pneumonia, bronchitis, ear infection, ear ache and death.

22. The method of claim 17, wherein the influenza A virus is an H7N7 subtype.

23. A method for quantifying an immunogenic agent of an influenza A H7 subtype virus in a vaccine comprising an immunogenic agent of the influenza A H7subtype virus, the method comprises contacting the vaccine with a first antibody, wherein the first antibody is the monoclonal antibody or antibody fragment of claim 1, and determining the amount of the immunogenic agent in the vaccine.

24. The method of claim 23, which further comprises contacting the specimen with a second antibody that specifically binds to an epitope of H7 hemagglutinin of the influenza A H7 subtype virus, wherein said second antibody contains or is conjugated to a detectable element.

25. The method of claim 24, wherein the first antibody is immobilized onto a solid surface.

26. The method of claim 24, wherein the second antibody contains a radioactive atom, is conjugated to a fluorescent molecule, or is conjugated to an enzyme.

27. The method of claim 23, wherein the immunogenic agent comprises an H7 hemagglutinin or antigenic portion thereof.

28. The method of claim 27, wherein the immunogenic agent is expressed by an expression system.

29. The method of claim 28, wherein the expression system is a viral expression vector and the immunogenic agent is presented or displayed on the surface of a virus produced by the viral expression vector.

30. A kit for identifying and/or quantifying an immunogenic agent of an influenza A H7 subtype virus in a patient's sample or in a vaccine comprising an immunogenic agent of the influenza A H7 subtype virus, which kit comprises a first antibody, wherein the first antibody is the monoclonal antibody or antibody fragment of claim 1 together with instructions for performing an assay to identify and/or quantify the immunogenic agent of the influenza A H7 subtype virus in the patient's sample or in the vaccine.

31. The kit of claim 30, which further comprises a second antibody that specifically binds to an epitope of H7 hemagglutinin of the influenza A H7 subtype virus, wherein said second antibody contains or is conjugated to a detectable element.

32. The kit of claim 31, wherein the first antibody is one of monoclonal antibody 11B9 or monoclonal antibody 62 and the second antibody is the other of said monoclonal antibody 11B9 or monoclonal antibody 62.

33. The kit of claim 30, wherein the second antibody contains a radioactive atom, is conjugated to a fluorescent molecule, or is conjugated to an enzyme.

34. A method for detecting an antibody against an influenza A H7 subtype virus in a biological specimen which comprises: (1) contacting a mixture of the specimen and a control H7 hemagglutinin antigen with a first antibody, wherein the first antibody is the monoclonal antibody or antibody fragment of claim 1; and (2) determining the presence or absence of an antibody against an influenza A H7 subtype virus.

35. The method of claim 34, which further comprises contacting the specimen with a second antibody that specifically binds to an epitope of the control H7hemagglutinin antigen, wherein said second antibody contains or is conjugated to a detectable element, wherein the contacting with the second antibody is performed before the determination.

36. The method of claim 35, wherein the first antibody is immobilized onto a solid surface.

37. The method of claim 35, wherein the first antibody is one of monoclonal antibody 11B9 or monoclonal antibody 62 and the second antibody is the other of said monoclonal antibody 11B9 or monoclonal antibody 62.

38. The method of claim 35, wherein the second antibody contains a radioactive atom, is conjugated to a fluorescent molecule, or is conjugated to an enzyme.

39. A kit for detecting an antibody against an influenza A H7 subtype virus in a biological specimen which comprises a first antibody, wherein the first antibody is the monoclonal antibody or antibody fragment of claim 1 together with instructions for performing an assay to detect the antibody against an influenza A H7 subtype virus.

40. The kit of claim 39, which further comprises a control hemaglutinin antigen.

41. The kit of claim 39, which further comprises a second antibody that specifically binds to an epitope of the control H7 hemagglutinin antigen, wherein said second antibody contains or is conjugated to a detectable element.

42. The kit of claim 41, wherein the first antibody is immobilized onto a solid surface.

43. The kit of claim 41, wherein the first antibody is one of monoclonal antibody 11B9 or monoclonal antibody 62 and the second antibody is the other of said monoclonal antibody 11B9 or monoclonal antibody 62.

44. The kit of claim 41, wherein the second antibody contains a radioactive atom, is conjugated to a fluorescent molecule, or is conjugated to an enzyme.

45. A method for detecting the presence of influenza A H7 antigen or anti-H7antibodies in a biological specimen which comprises:
  (a) contacting a sample with a capture antibody bound to a solid phase, wherein the capture antibody binds H7 antigen and is one of monoclonal antibody 11B9 as produced by hybridoma 11B9 which is deposited with Cell Bank Australia with Accession Number CBA20120022 or monoclonal antibody 62 as produced by hybridoma 62 which is deposited with Cell Bank Australia with Accession Number CBA20120023;
  (b) contacting the solid phase of (a) with a detector antibody, wherein the detector antibody binds H7 antigen and is the other of monoclonal antibody 11B9 or monoclonal antibody 62 containing or conjugated to a detectable element; and
  (c) determining the binding detector antibody or the amount of binding of the detector antibody,
  wherein
  (i) if the sample is a biological specimen that is not mixed with control H7 antigen prior to contacting with the capture antibody, bound detector antibody is indicative of the presence of influenza A H7 antigen in the biological specimen, and
  (ii) if the sample is a biological specimen that is mixed with control H7 antigen prior to contacting with the capture antibody, bound detector antibody is indicative of the presence of anti-H7 antibodies in the biological specimen.

46. A kit for detecting the presence of influenza A H7 antigen or anti-H7antibodies in a biological specimen which comprises
  (a) a first antibody which is a capture antibody, wherein the first antibody binds H7antigen and is one of monoclonal antibody 11B9 as produced by hybridoma 11B9 which is deposited with Cell Bank Australia with Accession Number CBA20120022 or monoclonal antibody 62 as produced by hybridoma 62 which is deposited with Cell Bank Australia with Accession Number CBA20120023;
  (b) a second antibody which is a detector antibody, wherein the second antibody binds H7 antigen and is the other of monoclonal antibody 11B9 or monoclonal antibody 62containing or conjugated to a detectable element; and
  (c) instructions for performing an assay to detect influenza A H7 antigen or anti-H7antibodies.

47. The kit of claim 46, which further comprises a control H7 antigen.

* * * * *

SEQUENCE LISTING

```
<160> NUMBER OF SEQ ID NOS: 2

<210> SEQ ID NO 1
<211> LENGTH: 1689
<212> TYPE: DNA
<213> ORGANISM: Influenza virus
<220> FEATURE:
<221> NAME/KEY: CDS
<222> LOCATION: (1)..(1689)

<400> SEQUENCE: 1 atg aac act caa atc ctg gta ttc gct ctg gtg gcg agc att ccg aca       48
Met Asn Thr Gln Ile Leu Val Phe Ala Leu Val Ala Ser Ile Pro Thr
1               5                   10                  15 aat gca gac aag atc tgc ctt ggg cat cat gcc gtg tca aac ggg act       96
Asn Ala Asp Lys Ile Cys Leu Gly His His Ala Val Ser Asn Gly Thr
            20                  25                  30 aaa gta aac aca tta act gag aga gga gtg gaa gtc gtt aat gca act      144
Lys Val Asn Thr Leu Thr Glu Arg Gly Val Glu Val Val Asn Ala Thr
        35                  40                  45
```

```
gaa acg gtg gaa cga aca aac gtt ccc agg atc tgc tca aaa ggg aaa    192
Glu Thr Val Glu Arg Thr Asn Val Pro Arg Ile Cys Ser Lys Gly Lys
 50                  55                  60 agg aca gtt gac ctc ggt caa tgt gga ctt ctg gga aca atc act ggg    240
Arg Thr Val Asp Leu Gly Gln Cys Gly Leu Leu Gly Thr Ile Thr Gly
 65                  70                  75                  80 cca ccc caa tgt gac caa ttc cta gaa ttt tcg gcc gac tta att att    288
Pro Pro Gln Cys Asp Gln Phe Leu Glu Phe Ser Ala Asp Leu Ile Ile
                 85                  90                  95 gag agg cga gaa gga agt gat gtc tgt tat cct ggg aaa ttc gtg aat    336
Glu Arg Arg Glu Gly Ser Asp Val Cys Tyr Pro Gly Lys Phe Val Asn
            100                 105                 110 gaa gaa gct ctg agg caa att ctc aga gag tca ggc gga att gac aag    384
Glu Glu Ala Leu Arg Gln Ile Leu Arg Glu Ser Gly Gly Ile Asp Lys
        115                 120                 125 gag aca atg gga ttc acc tac agc gga ata aga act aat gga aca acc    432
Glu Thr Met Gly Phe Thr Tyr Ser Gly Ile Arg Thr Asn Gly Thr Thr
130                 135                 140 agt gca tgt agg aga tca gga tct tca ttc tat gca gag atg aaa tgg    480
Ser Ala Cys Arg Arg Ser Gly Ser Ser Phe Tyr Ala Glu Met Lys Trp
145                 150                 155                 160 ctc ctg tca aac aca gac aat gct gct ttc ccg caa atg act aag tca    528
Leu Leu Ser Asn Thr Asp Asn Ala Ala Phe Pro Gln Met Thr Lys Ser
                165                 170                 175 tac aag aac aca agg aaa gac cca gct ctg ata ata tgg ggg atc cac    576
Tyr Lys Asn Thr Arg Lys Asp Pro Ala Leu Ile Ile Trp Gly Ile His
            180                 185                 190 cat tcc gga tca act aca gaa cag acc aag cta tat ggg agt gga aac    624
His Ser Gly Ser Thr Thr Glu Gln Thr Lys Leu Tyr Gly Ser Gly Asn
        195                 200                 205 aaa ctg ata aca gtt ggg agt tct aat tac caa cag tcc ttt gta ccg    672
Lys Leu Ile Thr Val Gly Ser Ser Asn Tyr Gln Gln Ser Phe Val Pro
210                 215                 220 agt cca gga gcg aga cca caa gtg aat ggc caa tct gga aga att gac    720
Ser Pro Gly Ala Arg Pro Gln Val Asn Gly Gln Ser Gly Arg Ile Asp
225                 230                 235                 240 ttt cat tgg ctg ata cta aac cct aat gac acg gtc act ttc agt ttc    768
Phe His Trp Leu Ile Leu Asn Pro Asn Asp Thr Val Thr Phe Ser Phe
                245                 250                 255 aat ggg gcc ttc ata gct cca gac cgt gca agc ttt ctg aga ggg aag    816
Asn Gly Ala Phe Ile Ala Pro Asp Arg Ala Ser Phe Leu Arg Gly Lys
            260                 265                 270 tcc atg gga att cag agt gaa gta cag gtt gat gcc aat tgt gaa gga    864
Ser Met Gly Ile Gln Ser Glu Val Gln Val Asp Ala Asn Cys Glu Gly
        275                 280                 285 gat tgc tat cat agt gga ggg aca ata ata agt aat ttg ccc ttt cag    912
Asp Cys Tyr His Ser Gly Gly Thr Ile Ile Ser Asn Leu Pro Phe Gln
290                 295                 300 aac ata aat agc agg gca gta gga aaa tgt ccg aga tat gtt aag caa    960
Asn Ile Asn Ser Arg Ala Val Gly Lys Cys Pro Arg Tyr Val Lys Gln
305                 310                 315                 320 gag agt ctg ctg ttg gca aca gga atg aag aat gtt ccc gaa atc cca   1008
Glu Ser Leu Leu Leu Ala Thr Gly Met Lys Asn Val Pro Glu Ile Pro
                325                 330                 335 aag agg agg agg aga ggc cta ttt ggt gct ata gcg ggt ttc att gaa   1056
Lys Arg Arg Arg Arg Gly Leu Phe Gly Ala Ile Ala Gly Phe Ile Glu
            340                 345                 350 aat gga tgg gaa ggt ttg att gat ggg tgg tat ggc ttc agg cat caa   1104
Asn Gly Trp Glu Gly Leu Ile Asp Gly Trp Tyr Gly Phe Arg His Gln
```

```
                355                 360                 365
aat gca caa ggg gag gga act gct gca gat tac aaa agc acc caa tca    1152
Asn Ala Gln Gly Glu Gly Thr Ala Ala Asp Tyr Lys Ser Thr Gln Ser
        370                 375                 380 gca att gat caa ata aca ggg aaa tta aat cgg ctt ata gaa aaa act    1200
Ala Ile Asp Gln Ile Thr Gly Lys Leu Asn Arg Leu Ile Glu Lys Thr
385                 390                 395                 400 aac caa cag ttt gag tta ata gac aac gaa ttc act gag gtt gaa agg    1248
Asn Gln Gln Phe Glu Leu Ile Asp Asn Glu Phe Thr Glu Val Glu Arg
                405                 410                 415 caa att ggc aat gtg ata aac tgg acc aga gat tcc atg aca gaa gtg    1296
Gln Ile Gly Asn Val Ile Asn Trp Thr Arg Asp Ser Met Thr Glu Val
            420                 425                 430 tgg tcc tat aac gct gaa ctc tta gta gca atg gag aat cag cac aca    1344
Trp Ser Tyr Asn Ala Glu Leu Leu Val Ala Met Glu Asn Gln His Thr
        435                 440                 445 att gat ctg gcc gac tca gaa atg aac aaa ctg tac gaa cga gtg aag    1392
Ile Asp Leu Ala Asp Ser Glu Met Asn Lys Leu Tyr Glu Arg Val Lys
450                 455                 460 aga caa ctg aga gag aat gcc gaa gaa gat ggc act ggt tgc ttc gaa    1440
Arg Gln Leu Arg Glu Asn Ala Glu Glu Asp Gly Thr Gly Cys Phe Glu
465                 470                 475                 480 ata ttt cac aag tgt gat gac gac tgc atg gcc agt att aga aac aac    1488
Ile Phe His Lys Cys Asp Asp Asp Cys Met Ala Ser Ile Arg Asn Asn
                485                 490                 495 acc tat gat cac agc aag tac agg gaa gaa gca ata caa aat aga ata    1536
Thr Tyr Asp His Ser Lys Tyr Arg Glu Glu Ala Ile Gln Asn Arg Ile
            500                 505                 510 cag att gac cca gtc aaa cta agc agc ggc tac aaa gat gtg ata ctt    1584
Gln Ile Asp Pro Val Lys Leu Ser Ser Gly Tyr Lys Asp Val Ile Leu
        515                 520                 525 tgg ttt agc ttc ggg gca tca tgt ttc ata ctt ctg gcc att gca atg    1632
Trp Phe Ser Phe Gly Ala Ser Cys Phe Ile Leu Leu Ala Ile Ala Met
    530                 535                 540 ggc ctt gtc ttc ata tgt gtg aag aat gga aac atg cgg tgc act att    1680
Gly Leu Val Phe Ile Cys Val Lys Asn Gly Asn Met Arg Cys Thr Ile
545                 550                 555                 560 tgt ata taa                                                        1689
Cys Ile

<210> SEQ ID NO 2
<211> LENGTH: 562
<212> TYPE: PRT
<213> ORGANISM: Influenza virus

<400> SEQUENCE: 2

Met Asn Thr Gln Ile Leu Val Phe Ala Leu Val Ala Ser Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Thr Val Glu Arg Thr Asn Val Pro Arg Ile Cys Ser Lys Gly Lys
    50                  55                  60

Arg Thr Val Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95
```

```
Glu Arg Arg Glu Gly Ser Asp Val Cys Tyr Pro Gly Lys Phe Val Asn
            100                 105                 110

Glu Glu Ala Leu Arg Gln Ile Leu Arg Glu Ser Gly Ile Asp Lys
    115                 120                 125

Glu Thr Met Gly Phe Thr Tyr Ser Gly Ile Arg Thr Asn Gly Thr Thr
130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Asp Pro Ala Leu Ile Ile Trp Gly Ile His
                180                 185                 190

His Ser Gly Ser Thr Thr Glu Gln Thr Lys Leu Tyr Gly Ser Gly Asn
                195                 200                 205

Lys Leu Ile Thr Val Gly Ser Ser Asn Tyr Gln Gln Ser Phe Val Pro
    210                 215                 220

Ser Pro Gly Ala Arg Pro Gln Val Asn Gly Gln Ser Gly Arg Ile Asp
225                 230                 235                 240

Phe His Trp Leu Ile Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
                260                 265                 270

Ser Met Gly Ile Gln Ser Gly Val Gln Val Asp Ala Asn Cys Glu Gly
                275                 280                 285

Asp Cys Tyr His Ser Gly Gly Thr Ile Ile Ser Asn Leu Pro Phe Gln
290                 295                 300

Asn Ile Asn Ser Arg Ala Val Gly Lys Cys Pro Arg Tyr Val Lys Gln
305                 310                 315                 320

Glu Ser Leu Leu Leu Ala Thr Gly Met Lys Asn Val Pro Glu Ile Pro
                325                 330                 335

Lys Arg Arg Arg Arg Gly Leu Phe Gly Ala Ile Ala Gly Phe Ile Glu
                340                 345                 350

Asn Gly Trp Glu Gly Leu Ile Asp Gly Trp Tyr Gly Phe Arg His Gln
                355                 360                 365

Asn Ala Gln Gly Glu Gly Thr Ala Ala Asp Tyr Lys Ser Thr Gln Ser
370                 375                 380

Ala Ile Asp Gln Ile Thr Gly Lys Leu Asn Arg Leu Ile Glu Lys Thr
385                 390                 395                 400

Asn Gln Gln Phe Glu Leu Ile Asp Asn Glu Phe Thr Glu Val Glu Arg
                405                 410                 415

Gln Ile Gly Asn Val Ile Asn Trp Thr Arg Asp Ser Met Thr Glu Val
                420                 425                 430

Trp Ser Tyr Asn Ala Glu Leu Leu Val Ala Met Glu Asn Gln His Thr
                435                 440                 445

Ile Asp Leu Ala Asp Ser Glu Met Asn Lys Leu Tyr Glu Arg Val Lys
                450                 455                 460

Arg Gln Leu Arg Glu Asn Ala Glu Glu Asp Gly Thr Gly Cys Phe Glu
465                 470                 475                 480

Ile Phe His Lys Cys Asp Asp Cys Met Ala Ser Ile Arg Asn Asn
                485                 490                 495

Thr Tyr Asp His Ser Lys Tyr Arg Glu Glu Ala Ile Gln Asn Arg Ile
                500                 505                 510

Gln Ile Asp Pro Val Lys Leu Ser Ser Gly Tyr Lys Asp Val Ile Leu
```

-continued

```
                515                 520                 525
Trp Phe Ser Phe Gly Ala Ser Cys Phe Ile Leu Leu Ala Ile Ala Met
        530                 535                 540

Gly Leu Val Phe Ile Cys Val Lys Asn Gly Asn Met Arg Cys Thr Ile
545                 550                 555                 560

Cys Ile
```